US008049025B2

(12) United States Patent
Zhan

(10) Patent No.: US 8,049,025 B2
(45) Date of Patent: Nov. 1, 2011

(54) RECYCLABLE RUTHENIUM CATALYSTS FOR METATHESIS REACTIONS

(75) Inventor: Zheng-Yun James Zhan, Shanghai (CN)

(73) Assignee: Zannan Scitech Co., Ltd., Shanghai (CN)

( * ) Notice: Subject to any disclaimer, the term of this patent is extended or adjusted under 35 U.S.C. 154(b) by 16 days.

(21) Appl. No.: 12/604,818

(22) Filed: Oct. 23, 2009

(65) Prior Publication Data

US 2010/0041844 A1   Feb. 18, 2010

Related U.S. Application Data

(63) Continuation of application No. 11/478,610, filed on Jul. 3, 2006, now Pat. No. 7,632,772.

(30) Foreign Application Priority Data

Jul. 4, 2005   (CN) .......................... 2005 1 0080379

(51) Int. Cl.
*C07F 15/00* (2006.01)
*C07C 2/02* (2006.01)
(52) U.S. Cl. ............... 556/13; 585/527; 548/402; 546/2
(58) Field of Classification Search .................. 585/527; 556/13; 548/402; 546/2
See application file for complete search history.

(56) References Cited

U.S. PATENT DOCUMENTS

| 6,921,735 | B2 | 7/2005 | Hoveyda et al. |
| 2002/0107138 | A1 | 8/2002 | Hoveyda et al. |
| 2003/0220512 | A1 | 11/2003 | Blechert |
| 2005/0143580 | A1 | 6/2005 | Arlt |

FOREIGN PATENT DOCUMENTS

| WO | WO 96/04289 | 2/1996 |
| WO | WO 00/71554 | 11/2000 |
| WO | WO 02/14376 | 2/2002 |
| WO | WO 2004/035596 | 4/2004 |

OTHER PUBLICATIONS

S.J. Connon, et al., "Recent Developments in Olefin Cross-Metathesis", Angew. Chem. Int. Ed., vol. 42, 2003, pp. 1900-1923.
K. Grela, et al., "A Highly Efficient Ruthenium Catalys For Metathesis Reactions", Angew. Chem. Ed., vol. 41, 2002, pp. 4038-4040.
Q. Yao, "A Soluble Polymer-Bound Ruthenium Carbene Complex: A Robust and Reusable Catalyst For Ring-Closing Olefin Metathesis", Angew. Chem. Int. Ed., vol. 39, 2000, pp. 3896-3898.
S. C. Schuerer, et al., "Synthesis and Application of a Permanently Immobilized Olefin-Metathesis Catalyst", Angew. Chem. Int. Ed., vol. 39, 2000, pp. 3898-3901.
H. Wakamatsu, et al., "A Highly Active and Air-Stable Ruthenium Complex For Olefin Metathesis", Angew. Chem. Int. Ed., vol. 41, 2002, pp. 794-796.
S.J. Connon, et al., "A Solid-Supported Phosphine-Free Ruthenium Alkylidene For Olefin Metathesis in Methanol and Water", Bioorganic & Medicinal Chemistry Letters, vol. 12, 2002 p. 1873-1876.
J. S. Kingsbury, et al., "A Recyclable Ru-Based Metathesis Catalyst", J. Am. Chem. Soc., vol. 121, 1999, pp. 791-799.
J. J. Van Veldhuizen, et al., "A Recyclable Chiral Ru Catalyst for Enantioselective Olefin Metathesis. Efficient Catallytic Asymmetric Ring-Opening/Cross Metathesis in Air", J. Am. Chem. Soc., vol. 124, 2002, pp. 4954-4955.
A.K. Chatterjee, et al., "Synthesis of Trisubstituted Alkenes via Olefin Cross-Metathesis", Organic Letters, vol. 1, No. 11, 1999, pp. 1751-1753.
C. W. Lee, et al., "Stereoselectivity of Macrocyclic Ring-Crossing Olefin Metathesis", Organic Letters, vol. 2, No. 14, 2000, pp. 2145-2147.
T. M. Trinka, et al., "The Development of $L_2X_2Ru=CHR$ Olefin Metathesis Catalysts: An Organometallic Success Story", Accounts of Chemical Research, vol. 34, No. 1, 2001, pp. 18-29.
S.J. Connon, et al., "A Self-Generating, Highly Active, and Recyclable Olefin-Metathesis Catalyst", Angew. Chem. Int. Ed., vol. 41, 2002, pp. 3835-3838.
S.T. Nguyen, et al., "Ring-Opening Metathesis Polymerization (ROMP) of Norbornene by a Group VIII Carbene Complex in Protic Media", J. Am. Chem. Soc., 1992, vol. 114, pp. 3974-3975.
M. Scholl, et al., "Synthesis and Activity of a New Generation of Ruthenium-Based Olefin Metathesis Catalysts Coordinated with 1,3-Dimesityl-4,5-dihydroimidazol-2-ylidene Ligands5", Organic Letters, 1999, vol. 1, No. 6, pp. 953-956.
S.B. Garber, et al., "Efficient and Recyclable Monomeric and Dendritic Ru-Based Metathesis Catalysts", J. Am. Chem. Soc., 2000, vol. 122, pp. 8168-8179.
F. Courchay, et al., "The Utility of Hoveyda-Type Catalysts in ADMET Chemistry: Sterics Versus Electronics", Journal of Molecular Catalysis A: Chemical, 254, 2006, pp. 111-117.
Z. Zhan, et al., "Significant substituent effect of ligand '2-isopropoxystyrene' on the activity and stability of Hoveyda-Grubbs catalysts for olefin metathesis", Abstract, 2005, ACS Sprint National Meeting.
J. Krause, et al., "Synthesis and Reactivity of Homonogeneous and Heterogeneous Ruthenium-Based Metathesis Catalysts Containing Electron-Withdrawing Ligands", Chem. Eur. J. 2004, vol. 10, pp. 777-784.
L. Yang, et al., "Novel Metathesis Catalysts Based on Ruthenium 1,3-Dimesityl-3,4,5,6-Tetrahydropyrimidin-2-Ylidenses: Synthesis, Structure, Immobilization, and Catalytic Activity", Chem. Eur. J. 2004, vol. 10, pp. 5761-5770.
J. Krause, et al., "Heterogenization of a Modified Grubbs-Hoveyda Catalyst on a ROMP-Derived Monolithic Support", Macromol. Rapid Commun., 2003, vol. 24, pp. 875-878.

*Primary Examiner* — Porfirio Nazario Gonzalez
(74) *Attorney, Agent, or Firm* — Oblon, Spivak, McClelland, Maier & Neustadt, L.L.P.

(57) ABSTRACT

The invention relates to novel carbene ligands and their incorporated monomeric and resin/polymer linked ruthenium catalysts, which are recyclable and highly active for olefin metathesis reactions. It is disclosed that significant electronic effect of different substituted 2-alkoxybenzylidene ligands on the catalytic activity and stability of corresponding carbene ruthenium complexes, some of novel ruthenium complexes in the invention can be broadly used as catalysts highly efficient for olefin metathesis reactions, particularly in ring-closing (RCM), ring-opening (ROM), ring-opening metathesis polymerization (ROMP) and cross metathesis (CM) in high yield. The invention also relates to preparation of new ruthenium complexes and the use in metathesis.

21 Claims, No Drawings

RECYCLABLE RUTHENIUM CATALYSTS FOR METATHESIS REACTIONS

This application is a Continuation of U.S. application Ser. No. 11/478,610, filed on Jul. 3, 2006, which is now allowed.

FIELD OF THE INVENTION

The present invention relates to novel ligands and their incorporated monomeric and resin/polymer linked ruthenium catalysts, which are recyclable and highly active for olefin metathesis reactions. The invention also relates to preparation of new ruthenium complexes and the use thereof in metathesis.

BACKGROUND OF THE INVENTION

The metathesis mechanism was proposed by 2005 Nobel laureates Yves Chauvin in the early 1970's. The metathesis reactions were practically carried out with transition metal catalysts in the 1990's by two other 2005 Nobel laureates, Robert H. Grubbs and Richard R. Schrock. Olefin metathesis catalyzed by transition metal carbene complexes is broadly employed in organic synthesis, particularly in drug discovery and development of polymeric materials and industrial syntheses. Since the 1990's, the metathesis reactions have been intensively studied and several kinds of valuable transition metal complexes have been reported as active metathesis catalysts, for examples, Grubbs et al., *J Am. Chem. Soc.* 1992, 114, 3974-3975, *Org. Lett.* 1999, 1, 953-956, WO 9604289 A1, WO 2000071554 A2, reported the first and second generation of Ru catalysts with good metathesis activity, but the Ru catalysts with tricyclohexylphosphine ligand is unstable in air and water, and the catalytic activity is not good enough for some multiple substituted olefin substrates. Hoveyda et al., *J. Am. Chem. Soc.* 1999, 121, 791-799, *J. Am. Chem. Soc.* 2000, 122, 8168-8179, US 20020107138 A1 and U.S. Pat. No. 6,921,735 B2, developed ruthenium complexes with new monomeric and dendritic alkoxybenzylidene ligand based Ru catalysts, which alkoxybenzylidene ligand based Ru catalysts offer higher activity and better stability in comparison to Grubbs Ru catalysts without alkoxybenzylidene ligands. Grela et al., *Angew. Chem. Int. Ed.* 2002, 41, 4038-4039, WO 04035596 A1, and Blechert et al., US20030220512 A1, improved the catalytic activity by incorporating some substituted alkoxybenzylidene ligands instead of Hoveyda's non-substituted alkoxybenzylidene ligands in metathesis reactions. However, a disadvantage of all reported Ru catalysts are obviously substrate-dependent for different kinds of reported ruthenium complexes in metathesis reactions with multiple functionally substituted substrates.

Currently, metathesis reactions have been becoming crucial steps in chemical and pharmaceutical industries. To overcome the activity and substrate-dependent problem, it is a goal to develop more active and recyclable catalysts as an alternative to some well-known catalysts for metathesis reactions, which could avoid the metal contamination of metathesis products and reduce the cost of ruthenium catalysts when the Ru catalysts are used in manufacturing.

SUMMARY OF THE INVENTION

The present invention involves novel carbene ligands and their monomeric and resin, PEG, polymer linked ruthenium complexes that can be used as highly active metathesis catalysts in RCM, CM, and ROMP. The metathesis catalysts are ruthenium complexes with different functionally substituted 'alkoxybenzylidene' carbene ligand, and the resin/polymer linked ruthenium complexes are chemically bounded on the surface of the resins, PEGs, and polymers that permit the reuse and recovery of the catalysts from the reaction mixture. The new ruthenium complexes of the invention can be in monomeric and polymeric forms that catalyze different kinds of metathesis reactions in a very efficient manner. The resin- and PEG-linked metathesis catalysts of the invention offer great advantage in recyclable utility, and leave little or no trace of toxic metal contamination within the product of olefin metathesis reactions. The catalysts have broad application in the chemical and pharmaceutical industries.

Thus, the present invention comprises novel Ru complexes of the following formula I, which has been evaluated to be highly active and efficient for metathesis reactions with multi-substituted olefin substrates and can be broadly used as an alternative to the existing catalysts.

In one aspect, the present invention provides a transition catalyst having the following structure I:

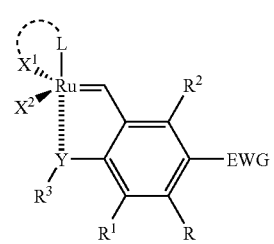

wherein:
$X^1$ and $X^2$ are the same or different and each selected from electron-withdrawing anionic ligands, and both $X^1$ and $X^2$ could be linked each other via the carbon-carbon and/or carbon-heteroatom bonds;

Y is a neutral two-electron donor selected from oxygen, sulfur, nitrogen or phosphorus;

R is H, halogen atom, alkyl, alkoxy, aryl, aryloxy, alkylcarbonyl, arylcarbonyl, alkoxycarbonyl, aryloxycarbonyl, heteroaryl, carboxyl ($RCO_2$—), cyano, nitro, amido, amino, aminosulfonyl, N-heteroarylsulfonyl, alkylsulfonyl, arylsulfonyl, alkylsulfinyl, arylsulfinyl, alkylthio, arylthio, or sulfonamido group;

$R^1$ and $R^2$ are each H, Br, I, alkyl, alkoxy, aryl, aryloxy, alkylcarbonyl, arylcarbonyl, alkoxycarbonyl, aryloxycarbonyl, carboxyl, amido, amino, heteroaryl, alkylthio, arylthio, or sulfonamido group;

$R^3$ is an alkyl, aryl, heteroaryl, alkylcarbonyl, arylcarbonyl, thiocarbonyl, or aminocarbonyl group;

EWG is an electron withdrawing group and selected from aminosulfonyl, amidosulfonyl, N-heteroarylsulfonyl, arylsulfonyl, arylsulfinyl, arylcarbonyl, alkylcarbonyl, aryloxycarbonyl, aminocarbonyl, amido, sulfonamido, chloro, fluoro, proton, or haloalkyl group; and L is an electron donating ligand, which could be linked with $X^1$ via the carbon-carbon and/or carbon-heteroatom bonds.

In preferred embodiment, $X^1$ and $X^2$ each is chloride (Cl), Y is oxygen (O), R is H, Cl, F, or $C_{1-8}$ alkoxycarbonyl group, $R^1$ and $R^2$ each is H, $R^3$ is a lower alkyl or aryl group, EWG is selected from $C_{1-12}$ N-alkylaminosulfonyl, $C_{4-12}$ N-heteroarylsulfonyl, $C_{4-12}$ aminocarbonyl, $C_{6-12}$ arylsulfonyl, $C_{1-12}$ alkylcarbonyl, $C_{6-12}$ arylcarbonyl, $C_{6-12}$ aryloxycarbonyl, Cl, F, or trifluoromethyl group, L is $PCy_3$ or $H_2IMes$.

In another aspect, the present invention also provides a composition comprising a transition catalyst having the following resin, PEG, and polymer linked structure IIIa-IIId (sometimes collectively referred to as "III"):

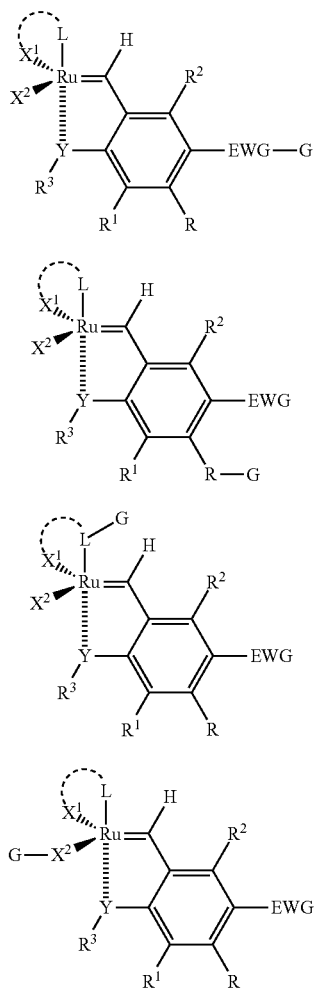

wherein:

G is a kind of support materials selected from resins, polymers, PEGs, or silica gel having amino, hydroxy, alkylthio, haloalkyl, or carboxylic group on the surface or terminal;

$X^1$, $X^2$, Y, $R^1$, $R^2$, $R^3$, L, EWG each is as defined in the structure I, respectively.

In preferred embodiment, G is resins, PEGs, or polymers having the amino or hydroxy group on the surface, $X^1$ and $X^2$ each is chloride (Cl), Y is oxygen (O), R is H, Cl, F, or $C_{1-8}$ alkoxycarbonyl group, $R^1$ and $R^2$ each is H, $R^3$ is a lower alkyl or aryl group, EWG is selected from $C_{1-12}$ N-alkylaminosulfonyl, $C_{4-12}$ N-heteroarylsulfonyl, $C_{4-12}$ aminocarbonyl, $C_{6-12}$ arylsulfonyl, $C_{1-12}$ alkylcarbonyl, $C_{6-12}$ arylcarbonyl, $C_{6-12}$ aryloxycarbonyl, Cl, F, or trifluoromethyl group, L is $H_2$IMes or $PCy_3$.

Details of the invention are set forth in the description of the new ligand synthesis and complex preparation below. The objects and advantages of the invention will be apparent from the description.

DETAILED DESCRIPTION OF THE INVENTION

The present invention comprises two novel classes of carbene ligands and ruthenium complexes as catalysts more active than prior reported metathesis catalysts and more efficient for olefin metathesis reactions. Moreover, the resin and polymer linked ruthenium complexes (formula III), prepared by loading the new ligands on surface of the resins and polymers via the coupling and/or substitution reactions, can be easily recovered and reused by simple filtration from the reaction mixture once the reaction is completed.

The metathesis catalysts of the present invention comprise novel monomeric ruthenium complexes having the structure of Formula I, and their corresponding resin and polymer linked catalysts having the structure of Formula III. The novel monomeric and resin/polymer-linked recyclable catalysts (1.0-5.0 mol %) can catalyze a variety of olefin metathesis reactions in high yield in DCM, DCE or toluene. The monomeric ruthenium catalysts can be recovered by precipitation in MeOH or other solvents, and the resin and polymer linked catalysts can be recovered easily from the reaction mixture by simple filtration.

Synthesis of the new alkoxybenzylidene ligands and ruthenium complexes for new carbene ligands and monomeric ruthenium complexes having the structure of Formula 2 can be prepared based on four of alternative procedures in the following Schemes 1-4, respectively. In Scheme 1, it was reported by M. Yamaguchi et al (*J. Org. Chem.* 1998, 63, 7298-7305) to carry out ortho-vinylation reaction regioselectively with ethyne and different substituted phenols to offer diversity of substituted 2-alkoxystyrene ligands (V).

Scheme 1:

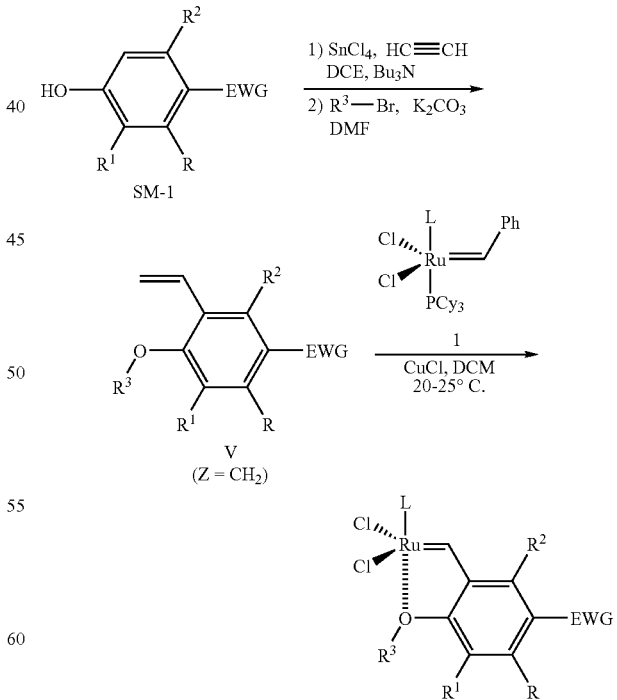

1a, 2a: L = $PCy_3$, Cy = Cyclohexyl
1b, 2b: L = $H_2$IMes (1,3-dimesityl-4,5-dihydroimidazol-2-ylidene)

Scheme 2:
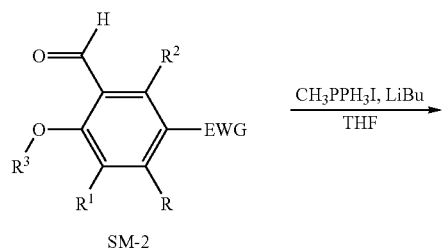
Scheme 3:
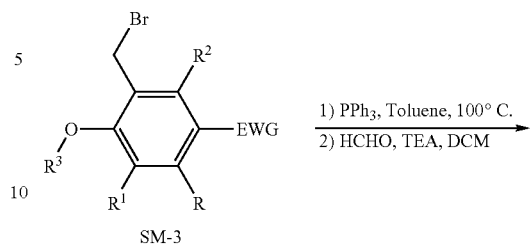
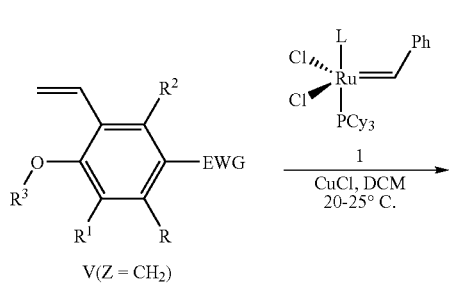
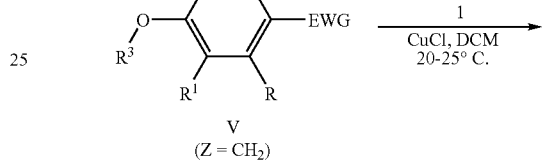
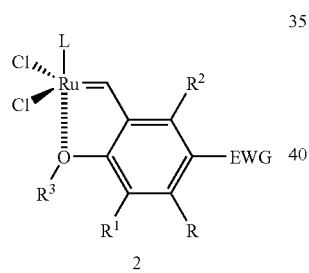
1a, 2a: L = PCy$_3$, Cy = Cyclohexyl
1b, 2b: L = H$_2$IMes (1,3-dimesityl-4,5-dihydroimidazol-2-ylidene)
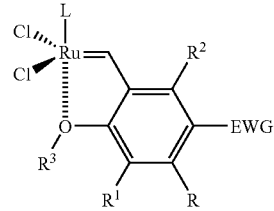
1a, 2a: L = PCy$_3$, Cy = Cyclohexyl
1b, 2b: L = H$_2$IMes (1,3-dimesityl-4,5-dihydroimidazol-2-ylidene)
Scheme 4:
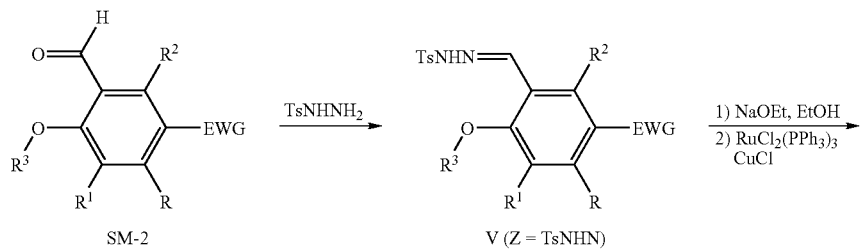

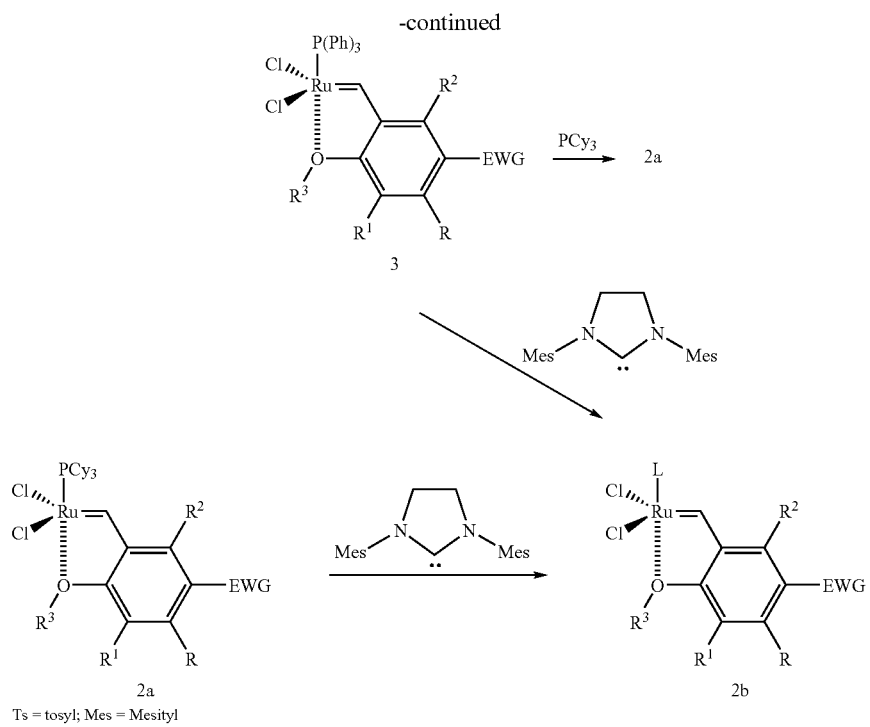

Ts = tosyl; Mes = Mesityl
2b: L = H₂IMes (1,3-dimesityl-4,5-dihydroimidazol-2-ylidene)

Based on four alternative synthetic procedures in Schemes 1-4, there are different kinds of substituted 2-alkoxystyrene ligands (V) and Ru complexes (2) prepared. Moreover, significant substituent effect of different substituted 2-alkoxybenzylidene ligands on the stability and activity of Ru complexes has been observed, and some novel Ru catalysts have been developed much more active than prior reported Ru catalysts for different kinds of metathesis reactions.

Significant Electronic effect of substituted 2-alkoxybenzylidene ligands on the stability of Ru complexes: To study the effect of substituted 2-alkoxybenzylidene ligands on the stability and activity of Ru complexes, different kinds of 3-substituted 2-alkoxybenzylidene ligands (4a-i) were prepared based on the procedure shown in Scheme 1. Surprisingly, during preparation of Ru complex with 3-$R^1$ substituted 2-isopropylbenzylidene ligand, when $R^1$ is an electron withdrawing group, it was failed to obtain some desired Ru complexes 5a-i via the following reported procedure in Scheme 5 (Hoveyda et al, *J. Am. Chem. Soc.* 1999, 121, 791-799, US20020107138).

Scheme 5:

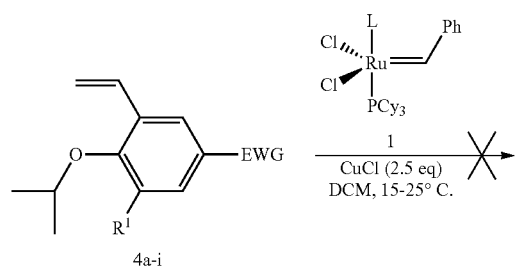

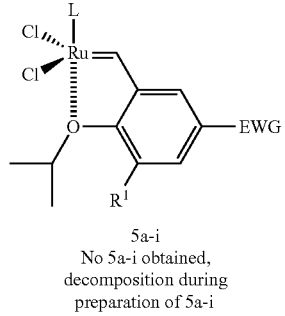

5a-i
No 5a-i obtained,
decomposition during
preparation of 5a-i

4a: $R^1$ = Cl, EWG = H; 1a: L = PCy₃;
4b: $R^1$ = Cl, EWG = H; 1b: L = H₂IMes;
4c: $R^1$ = Cl, EWG = Cl; 1a: L = PCy₃;
4d: $R^1$ = Cl, EWG = Cl; 1b: L = H₂IMes;
4e: $R^1$ = F, EWG = H; 1a: L = PCy₃;
4f: $R^1$ = F, EWG = H; 1b: L = H₂IMes;
4g: $R^1$ = CO₂Me, EWG = H; 1b: L = H₂IMes;
4h: $R^1$ = NO₂, EWG = H; 1b: L = H₂IMes;
4i: $R^1$ = SO₂NMe₂, EWG = H; 1b: L = H₂IMes;

It appears that 3-electron-withdrawing group substituted 2-isopropylbenzylidene ligands 4a-i result in the unexpected decomposition during preparation of Ru complexes 5a-i, which means that the electronic effect of 3-electron-withdrawing substituents on the stability of 5a-i is significant. Based on the significant electronic effect on the stability and catalytic activity of Ru complexes, it is possible to develop more active Ru catalysts by evaluating the electronic effect of different substituted 2-alkoxybenzylidene ligands on the stability and activity of Ru catalysts 7a-n as shown in Scheme 6. Based on synthetic Schemes 1-3, complexes 6a-n in Scheme 6 have been prepared in good yield, and the catalytic activity has been studied for several metathesis reactions with different multi-substituted olefin substrates 11 & 13.

Scheme 6:

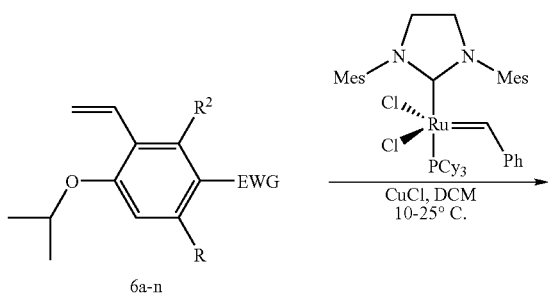

6a, 7a: R = H, R² = H, EWG = Cl;
6b, 7b: R = Cl, R² = H, EWG = Cl;
6c, 7c: R = H, R² = H, EWG = F;
6d, 7d: R = F, R² = H, EWG = F;
6e, 7e: R = F, R² = F, EWG = H;
6f, 7f: R = H, R² = H, EWG = CONH₂;
6g, 7g: R = H, R² = H, EWG = CO₂Me;
6h, 7h: R = H, R² = H, EWG = CHO
6i, 7i: R = H, R² = H, EWG = COCH₃;
6j, 7j: R = H, R² = H, EWG = COPh;
6k, 7k: R = H, R² = H, EWG = SO₂NMe₂;

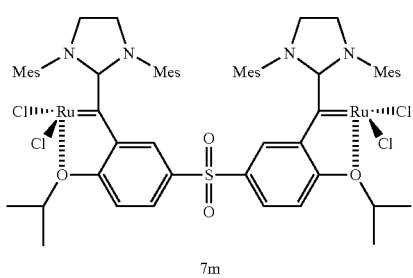

7m

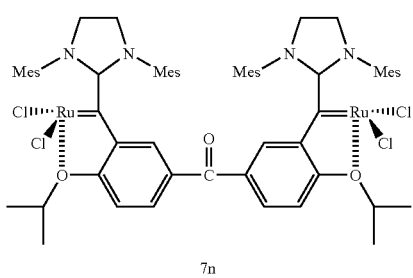

7n

All of 13 Ru complexes 7a-n have been evaluated for activity study by catalyzing the RCM reaction with substrate 11 in Equation 1, and the kinetic result for each catalyst is listed in Table 1. It was found that the novel catalyst 7k has the best activity of 13 studied complexes 7a-n with 5-EWG substituted 2-isopropoxybenzylidene ligands. Moreover, the Ru complexes with both 4-R and 5-EWG substituted ligands (e.g., 6b with 4,5-dichloro and 6b with difluoro substituted ligands) have better catalytic activity than the complexes with single 5-EWG substituted ligand, e.g., 6a and 6c, respectively. Based on the structure of catalyst 7k, it is more interested to develop more active Ru catalysts by preparing new Ru complexes (9a-j, Scheme 8) with diversity of novel 5-aminosulfonyl substituted 2-alkoxystyrene ligands 8a-j (Scheme 7) for activity study.

Scheme 7:

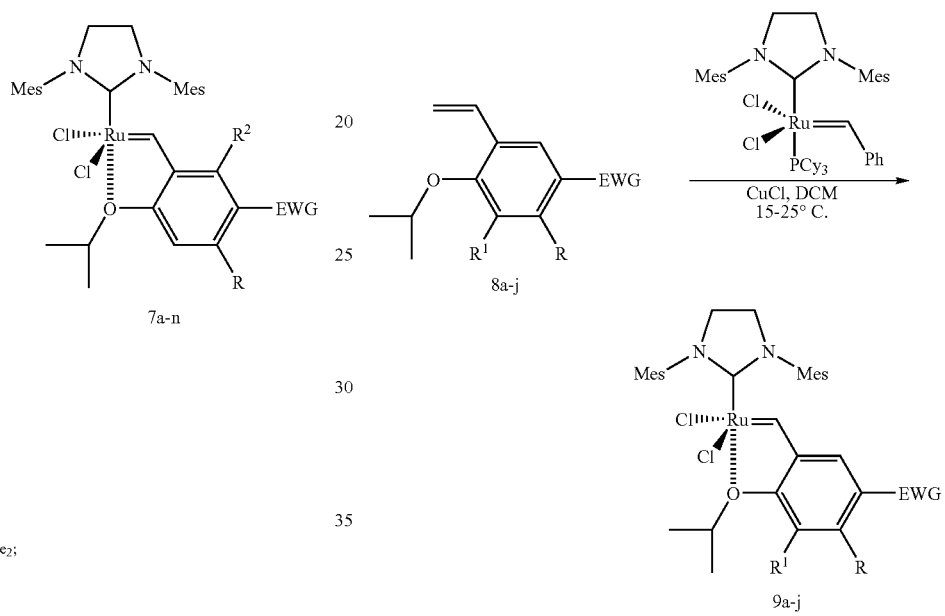

Scheme 8:

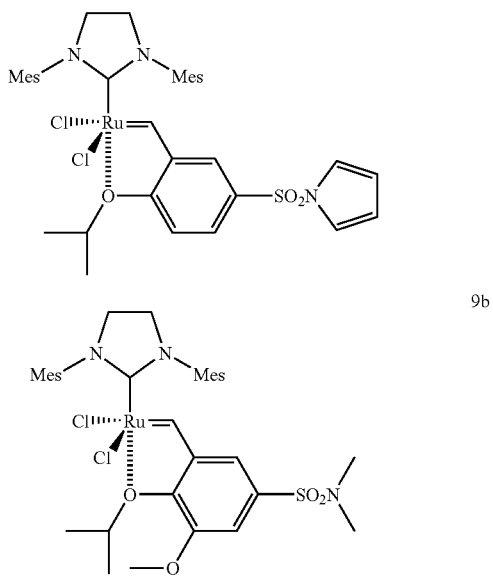

9c
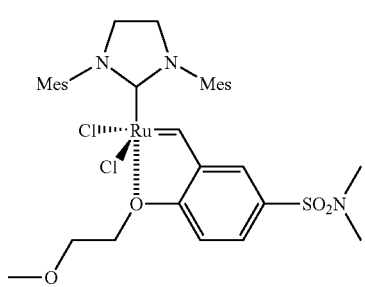
9d
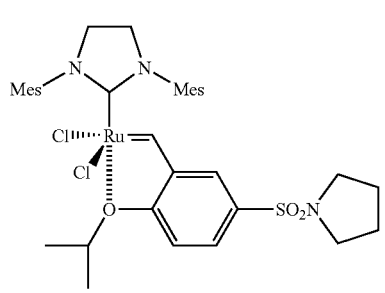
9e
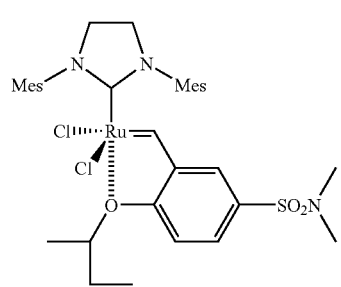
9f
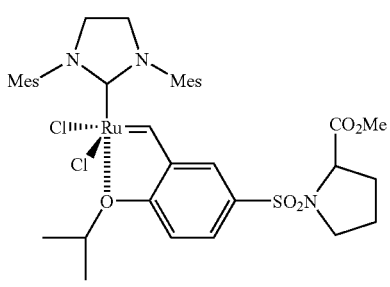
9g
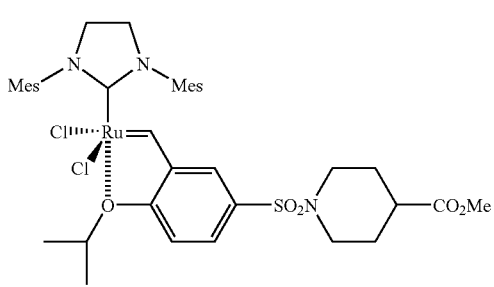
9h
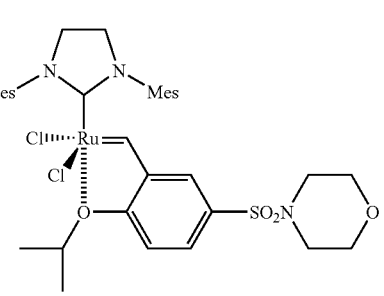
9i
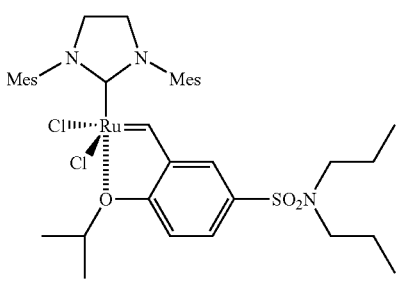
9j
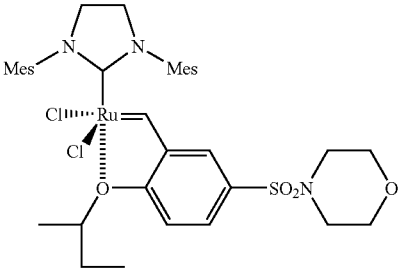
Scheme 9:
10a
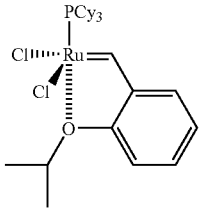
10b
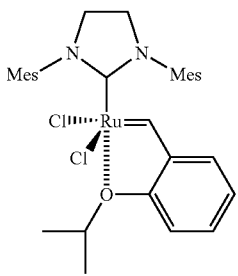

-continued

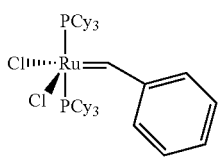
10c

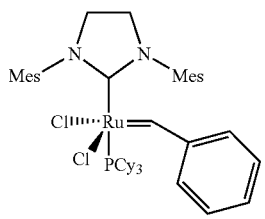
10d

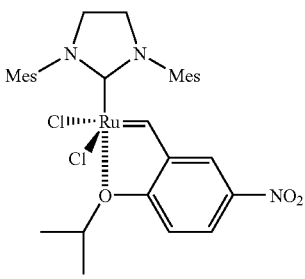
10e

To study the relative catalytic activity, two olefin substrates 11 an 13 in Equations 1 and 2 were selected for RCM reactions with different catalysts 7a-n, and 9a-j, respectively. Other five prior known Ru catalysts 10a-e in Scheme 9 (Hoveyda et al, *J. Am. Chem. Soc.* 1999, 121, 791-799, US20020107138, Grubbs et al., *J. Am. Chem. Soc.* 1992, 114, 3974-3975, *Org. Lett.* 1999, 1, 953-956, WO 9604289 A1, WO 2000071554 A2, Grela et al, *Angew. Chem. Int. Ed.* 2002, 41, 4038-4039, WO 04035596 A1) are also selected for the metathesis activity study of substrates 11 and 13 in comparison to all new Ru catalysts in the present invention. Because of the EWG and steric effect of both 1,5-dichloro and 3',3'-dimethyl-vinyl substituents on the metathesis reactions, the unique olefin substrate 13 is much more difficult than another common substrate 11 for Ru catalysts to catalyze the RCM reaction, so compound 13 is a better olefin substrate to be used for evaluation of more active metathesis catalysts. The experimental results of catalytic activity for different catalysts 7a-n, 9a-j and 10a-e are listed in Tables 1 & 2, respectively. Furthermore, when the phenyl is replaced with methyl at vinyl group of substrate 11, the RCM under the same catalyst condition is completed in shorter time, which means that the alkyl substituted olefin substrates are easier to carry out RCM reactions than the aryl substituted olefin substrates under the reaction condition in Equation 1.

TABLE 1

Activity Study of Ru Complexes for Substrate 11

Equation 1:

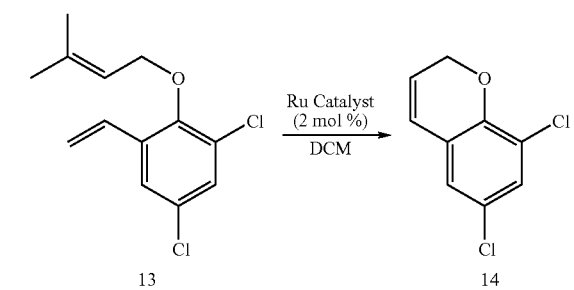

|  |  | Conversion (% by HPLC) | | | |
|---|---|---|---|---|---|
| Entry | Catalyst | 10 min | 30 min | 1.5 hr | 3.0 hr |
| 1 | 7a | 85 | 96 | 100 | |
| 2 | 7b | 88 | 100 | | |
| 3 | 7c | 81 | 87 | 94 | >97 |
| 4 | 7d | 83 | 91 | >97 | |
| 5 | 7e | 51 | 82 | 92 | 100 |
| 6 | 7f | 83 | 94 | 100 | |
| 7 | 7g | 84 | >97 | | |
| 8 | 7h | 87 | 98 | | |
| 9 | 7i | 88 | >97 | | |
| 10 | 7j | 90 | 98 | | |
| 11 | 7k | 91 | 100 | | |
| 12 | 7m | 89 | 94 | >98 | |
| 13 | 7n | 80 | 91 | 94 | >97 |
| 14 | 9g | 66 | 84 | 92 | >98 |
| 15 | 9h | 90 | 95 | 100 | |
| 16 | 9j | 82 | 91 | 97 | 100 |
| 17 | 10b | 71 | 88 | 95 | >97 |
| 18 | 10d | 12 | 23 | 37 | 81 |

TABLE 2

Metathesis Activity of Different Ru Complexes for Substrate 13

Equation 2:

|  |  | Conversion (% by HPLC) | | | | |
|---|---|---|---|---|---|---|
| Entry | Catalyst | 10 min | 30 min | 1.5 hr | 3.0 hr | Overnight |
| 1 | 7a | 26 | 51 | 76 | 86 | 100 |
| 2 | 7f | 28 | 54 | 89 | >98 | |
| 3 | 7i | 23 | 47 | 75 | 88 | >96 |

TABLE 2-continued

Metathesis Activity of Different Ru Complexes for Substrate 13

Equation 2:

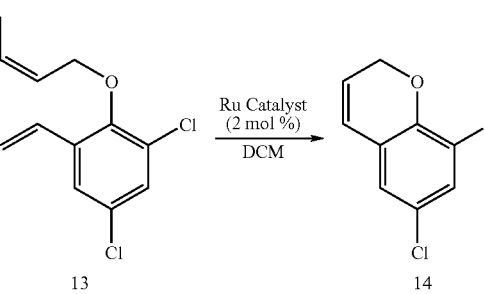

| Entry | Catalyst | Conversion (% by HPLC) | | | | |
|---|---|---|---|---|---|---|
| | | 10 min | 30 min | 1.5 hr | 3.0 hr | Overnight |
| 4 | 7k | 76 | 92 | 100 | | |
| 5 | 9a | 45 | 59 | 89 | 100 | |
| 6 | 9b | 85 | >98 | | | |
| 7 | 9c | 55 | 81 | 94 | 100 | |
| 8 | 9d | 31 | 49 | 67 | 84 | 100 |
| 9 | 9e | 48 | 82 | 94 | 100 | |
| 10 | 9f | 20 | 43 | 71 | 86 | >97 |
| 11 | 9g | 32 | 59 | 78 | 89 | 100 |
| 12 | 9h | 28 | 61 | 86 | 92 | 100 |
| 13 | 9i | 60 | 81 | 94 | >98 | |
| 14 | 9j | 32 | 60 | 79 | 86 | >97 |
| 15 | 19a | 2 | 5 | 23 | 46 | 100 |
| 16 | 19b | 7 | 28 | 61 | 75 | 100 |
| 17 | 10b | 9 | 18 | 32 | 63 | >95 |
| 18 | 10d | 3 | 7 | 16 | 52 | 92 |
| 19 | 10e | 49 | 77 | 89 | 100 | |

Based on the kinetic results, it is determined that some novel Ru catalysts (7k, 9a-9c, and 9i) with 5-dimethylaminosulfonyl and 5-(N-heteroarylsulfonyl) substituted 2-isopropoxybenzylidene ligand are very active catalysts and much more active than other evaluated Ru catalysts prior known catalysts 10a-e in Tables 1 & 2. Some of new catalysts 7a-n and 9a-j with 5-EWG (e.g., EWG=Cl, F, COAr, $CONH_2$, $SO_2Ar$, etc.) are also air-stable and highly active for different kinds of metathesis reactions. Based on the activity study in the present invention, the catalyst 9b is the most active catalysts of all surveyed Ru complexes, but it is not as stable as other catalysts with single 5-aminosulfonyl substituted 2-alkoxybenzylidene ligands, e.g., 7a, 7k, 9a, 9c and 9i. Based on the valuable results in Schemes 6, 7, 8 and Tables 1 & 2, several novel active Ru catalysts (e.g., 7a, 7b, 7e, 7f, 7j, 7k, 9a, 9c and 9i) can be broadly used in different kinds of metathesis reactions as an alternative to prior existing catalysts, and some novel catalysts with 5-aminosulfonyl-2-alkoxybenzylidene ligands (e.g., 7a, 7k, 9a, 9c and 9i) are more reactive and preferred for multi-substituted olefin substrates.

Resin/Polymer Supported Recyclable Ru Catalysts: To develop some recyclable and reusable Ru catalysts, two new Ru catalysts 9f and 9g with an ester group in Scheme 8 can be chemically bounded on the surface of support materials, e.g., resins, polymers, PEGs, and silica gel by the following new developed process for scale-up production in Scheme 10.

Scheme 10:

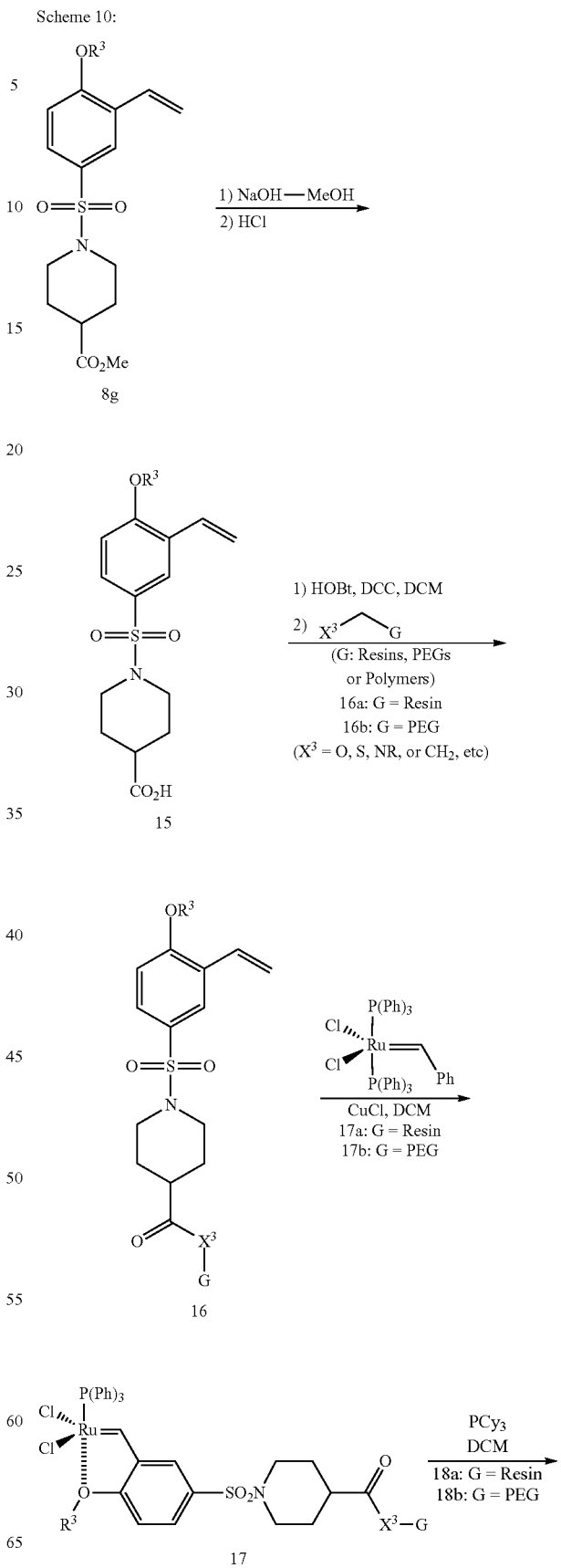

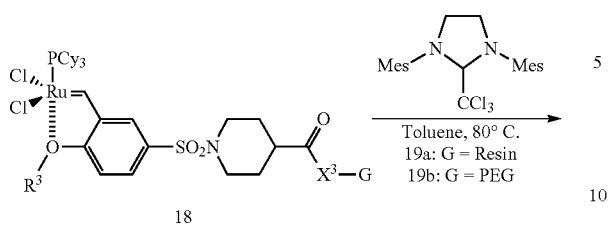

18

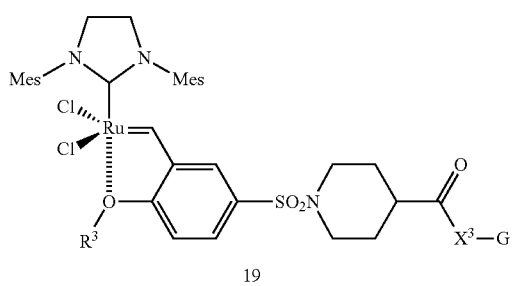

19

The resin and PEG linked Ru catalysts 19a and 19b have been evaluated for the relative activity for different metathesis reactions in Equations 3 & 4.

Equation 3:

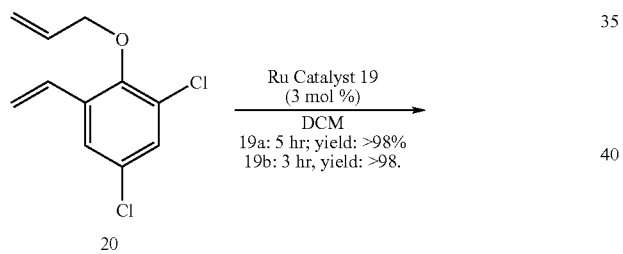

Equation 4:

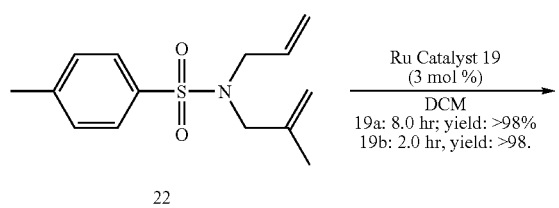

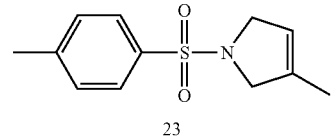

23

Resin linked Ru catalysts 18a and 19a are easily recovered by filtration and reusable for metathesis reactions effectively for 3-5 times, and both catalysts 18a and 19a also work well for less hindered olefin substrates 20 and 22. However, the resin linked Ru catalysts 18a and 19a do not work actively for substrate 13 because of the steric effect of dimethyl substituted vinyl group.

Cross metathesis (CM) has been also studied with styrene substrate 24 and Ru catalysts 9a and 9d in Equation 5. The CM product is regio-selective transisomer product 25 (>95% by $^1$HNMR).

Equation 5:

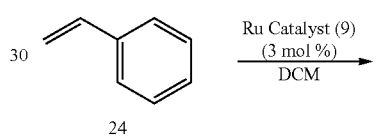

24

25

9a: Trans-isomer: >95% by $^1$HNMR
9d: Trans-isomer: >95% by $^1$HNMR

Two Alternative Production Procedures for Preparation of Some Highly Active Metathesis Catalysts with 5-EWG Substituted 2-Alkoxybenzylidene Ligands: As described in Scheme 4, based on some references and new process development, there are following two alternative procedures developed for scale-up production of different 5-EWG substituted 2-alkoxybenzylidene ligands. When EWG is Cl, F and H, it is no problem to prepare Ru complexes 7a and 7d directly by replacing ligand P(Ph)$_3$ of intermediate 28 with another ligand H$_2$IMes in Scheme 11. Each reaction product in Schemes 11 & 13 could be confirmed by determining the chemical shift change of $^1$HNMR, $^{31}$P-NMR, and/or $^{19}$F-NMR. The typical chemical shift changes of the isopropoxy and vinyl protons for each reaction product shown in Scheme 11 are listed in Scheme 12.

Scheme 11:
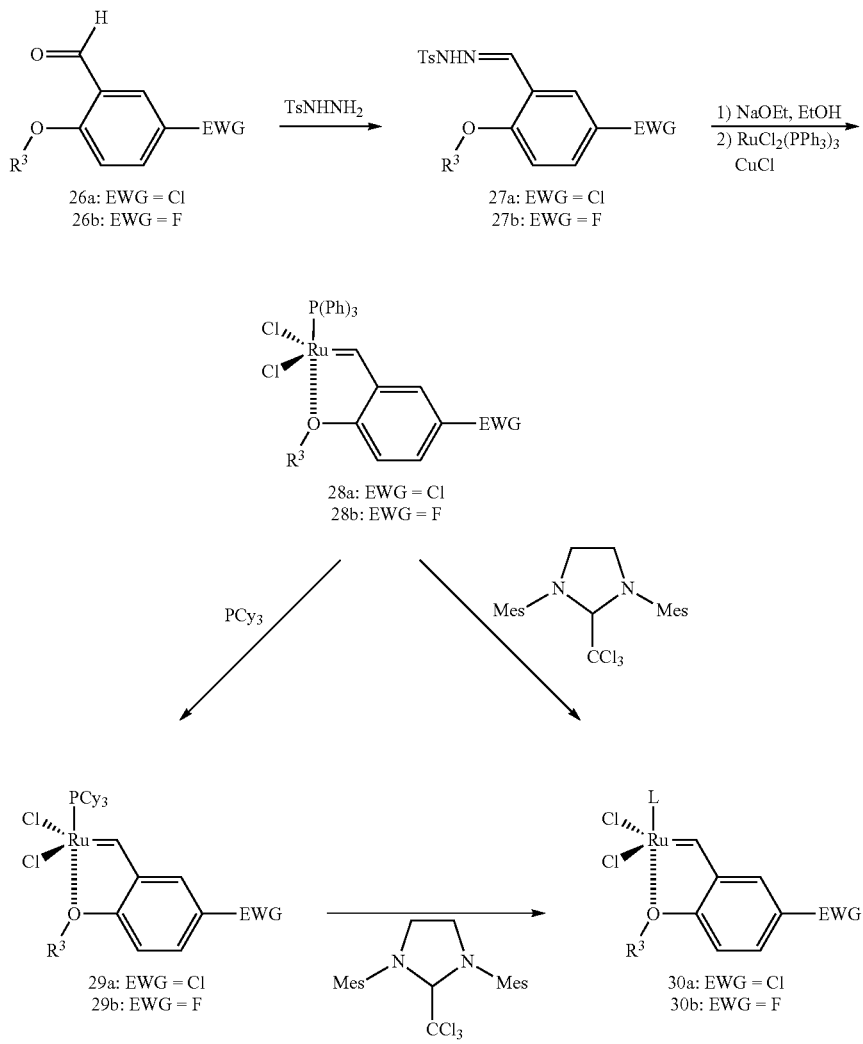
EWG = Cl, F, etc.; Ts = tosyl; R³ = isopropyl; Mes = Mesityl;
30: L = 1,3-dimesityl-4,5-dihydroimidazol-2-ylidene (H₂IMes)
(This procedure provides high yield from 28 to 30 when EWG is H)
Scheme 12:
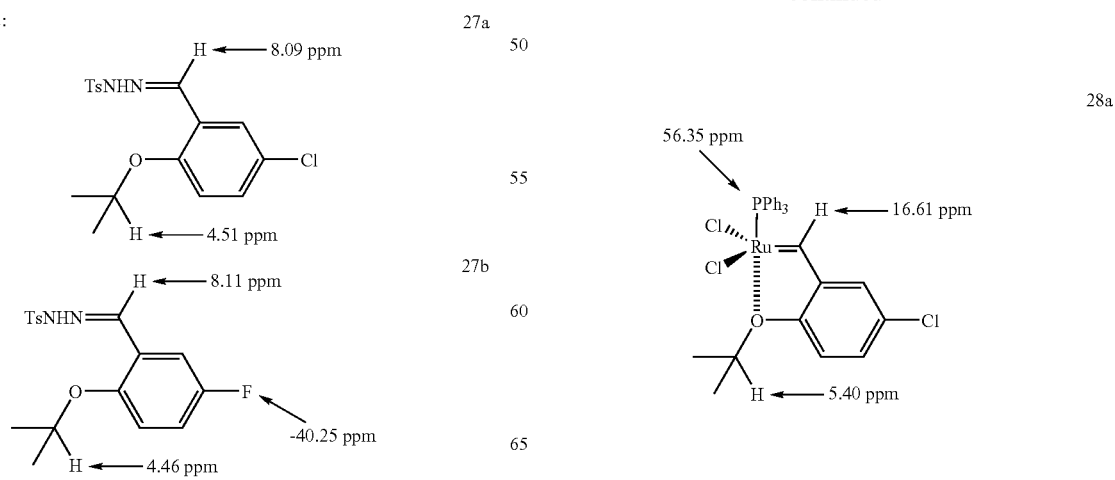

-continued

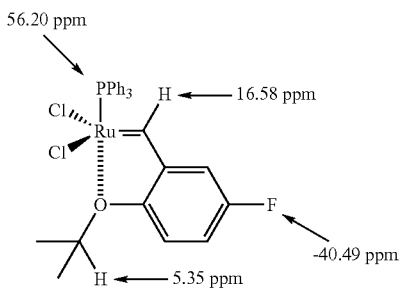
28b

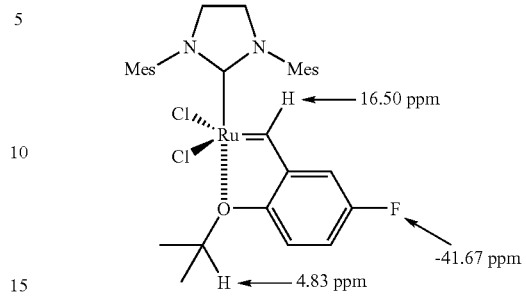
30b

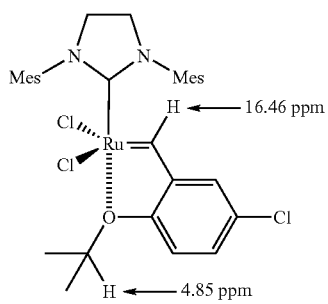
30a

However, the ligand P(Ph)$_3$ can not be directly replaced with ligand H$_2$IMes when EWG is SO$_2$NR$_2$ and NO$_2$. To prepare Ru complexes 7k and 10e when EWG is 5-SO$_2$NMe$_2$ and NO$_2$, respectively, it is required to replace the P(Ph)$_3$ of intermediate 33 with PCy$_3$ first, followed by substituting PCy$_3$ of intermediate 34 with H$_2$IMes to have the desired Ru complexes 7k and 10e prepared in good yield in Scheme 13. The typical chemical shift changes of the isopropoxy and vinyl/alkoxybenzylidene protons for each reaction product shown in Scheme 13 are listed in Scheme 14.

Scheme 13:

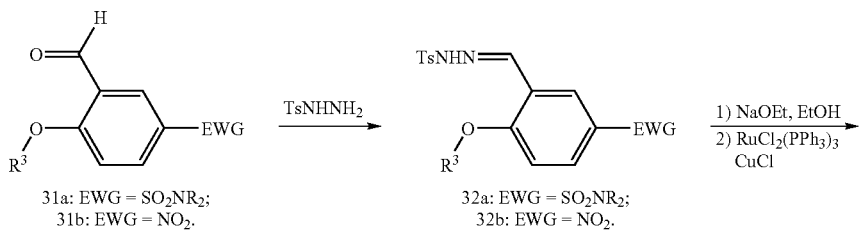

31a: EWG = SO$_2$NR$_2$;
31b: EWG = NO$_2$.

32a: EWG = SO$_2$NR$_2$;
32b: EWG = NO$_2$.

1) NaOEt, EtOH
2) RuCl$_2$(PPh$_3$)$_3$
   CuCl

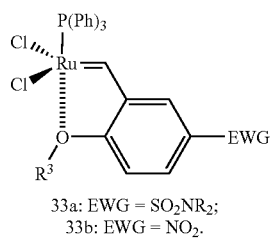

33a: EWG = SO$_2$NR$_2$;
33b: EWG = NO$_2$.

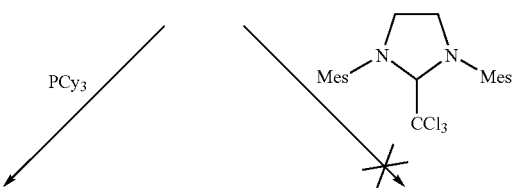

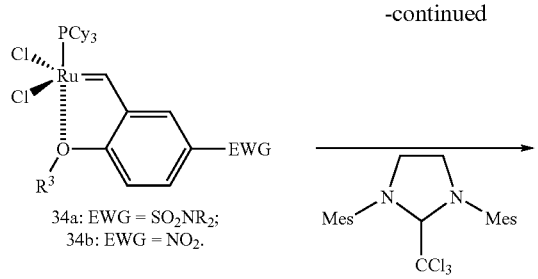
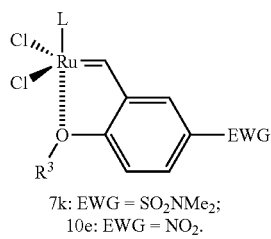
34a: EWG = SO$_2$NR$_2$;
34b: EWG = NO$_2$.
7k: EWG = SO$_2$NMe$_2$;
10e: EWG = NO$_2$.
EWG = NO$_2$, SO$_2$NR$_2$, etc.; Ts = tosyl; R$^3$ = iPr; Mes = Mesityl; L = 1,3-dimesityl-4,5-dihydroimidazol-2-ylidene (H$_2$IMes)
Scheme 14:
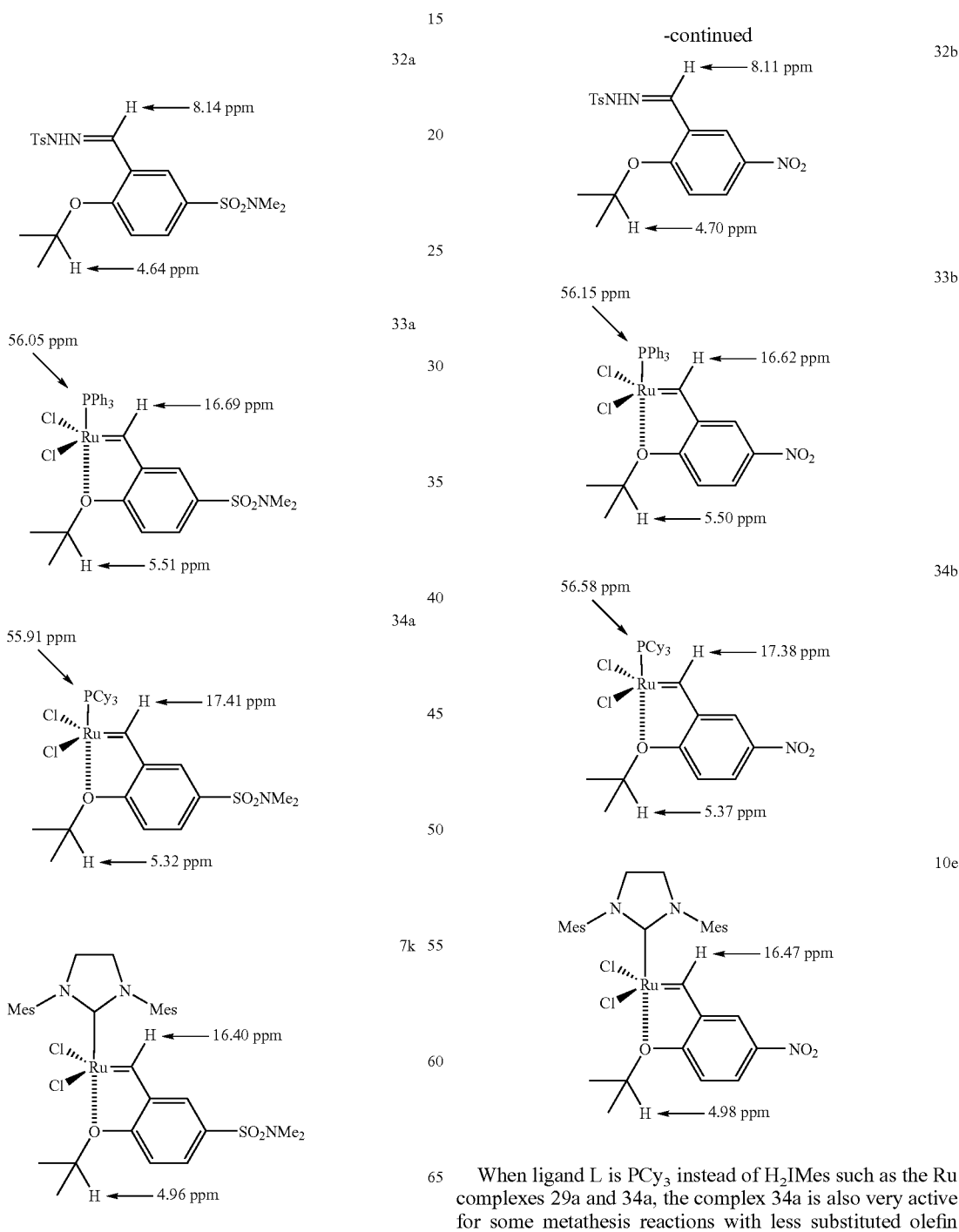
When ligand L is PCy$_3$ instead of H$_2$IMes such as the Ru complexes 29a and 34a, the complex 34a is also very active for some metathesis reactions with less substituted olefin substrates, e.g, compounds 36 and 38, but the activity and stability are not as good as the complex 7k and 9j with H$_2$IMes. Three new Ru complexes with different SO$_2$NR$_2$ and R$^3$ have been prepared in Scheme 15 and their activity has been studied in Equation 6, and metathesis results are listed in Tables 3 & 4.

Scheme 15:

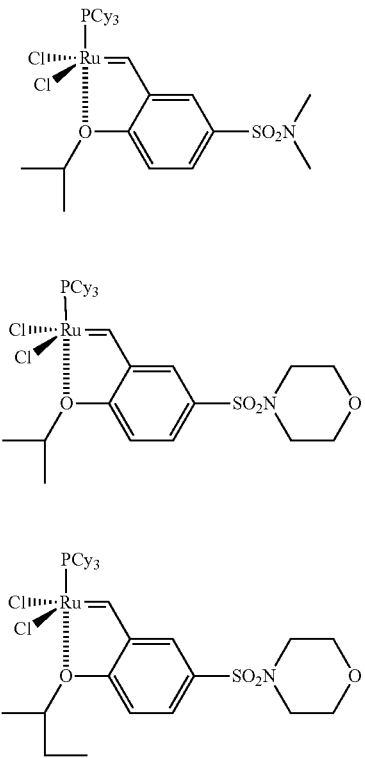

TABLE 3

Activity Study of New Ru Complexes for Subsrtate 36

Equation 6:

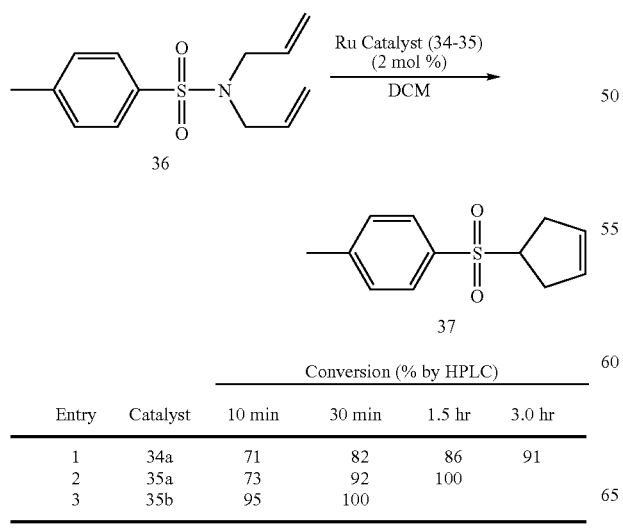

| Entry | Catalyst | Conversion (% by HPLC) | | | |
|---|---|---|---|---|---|
| | | 10 min | 30 min | 1.5 hr | 3.0 hr |
| 1 | 34a | 71 | 82 | 86 | 91 |
| 2 | 35a | 73 | 92 | 100 | |
| 3 | 35b | 95 | 100 | | |

TABLE 4

Activity Study of New Ru Complexes for Subsrtate 38

Equation 7:

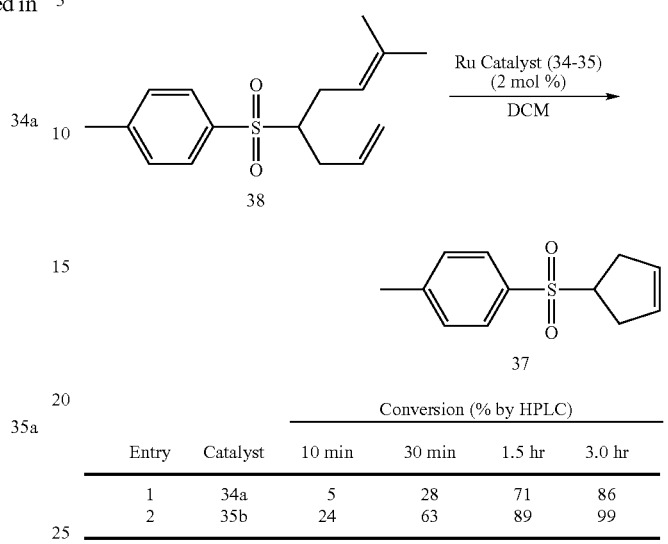

| Entry | Catalyst | Conversion (% by HPLC) | | | |
|---|---|---|---|---|---|
| | | 10 min | 30 min | 1.5 hr | 3.0 hr |
| 1 | 34a | 5 | 28 | 71 | 86 |
| 2 | 35b | 24 | 63 | 89 | 99 |

It suggests in Tables 3 & 4 that the new Ru catalyst 45b with PCy$_3$ ligand is more active than catalysts 34a and 35a.

Based on all observed results, it is founded that the Ru complexes with dialkylaminosulfonyl and N-heteroarylsulfonyl ligands such as 7k, 9a and 9b are a series of the most active metathesis catalysts in comparison with diversity of other different substituted 2-alkoxybenzylidene ligands, e.g., catalysts 7a-7j. On the other hand, Ru catalysts 7j, 7i, and 7f have good activity and much better than 10a-d.

Most of Ru catalysts 9a-j are soluble in DCM, DCE, CHCl$_3$, Ether, and other solvents, but almost insoluble in MeOH, EtOH, and other alcohols, which provides a recyclable method to recover the Ru catalysts 9a-j by precipitating the Ru catalysts in MeOH or EtOH. On the other hand, when the metathesis products are soluble in MeOH or EtOH, the Ru catalysts could be removed by precipitating the reaction mixture in MeOH. However, the Ru catalyst 7f with 5-aminocarbonyl-2-isopropylbenzylidene ligand is not only soluble in DCM, DCE, CHCl$_3$, Ether, and other solvents, but also soluble in MeOH, EtOH, and other alcohols, which suggests that it is better to use Ru catalyst 7f for metathesis reactions when the metathesis products are insoluble and precipitated in MeOH or EtOH, so the alcohol-soluble Ru catalyst 7f is easily removed in alcohol solution by filtration.

Finally, the resin-linked Ru catalysts 18a and 19a are not only highly active, but also recyclable and reusable efficiently for metathesis reactions for 3-6 times.

EXAMPLES

General. Infrared (1R) spectra were recorded on a Fourier Transform AVATAR™ 360 E.S.P™ spectrophotometer (Unit: cm$^{-1}$). Bands are characterized as broad (br), strong (s), medium (m), and weak (w). $^1$H NMR spectra were recorded on a Varian-400 (400 MHz) spectrometer. Chemical shifts are reported in ppm from tetramethylsilane with the solvent resonance as the internal standard (CDCl$_3$: 7.26 ppm). Data are reported as follows: chemical shift, multiplicity (s=singlet, d=doublet, t triplet, q=quartet, br=broad, m=multiplet), coupling constants (Hz), integration, and assignment. $^{19}$F and $^{31}$P NMR spectra were recorded on a Varian-400 (400 MHz) and Gemini-2000 (300 MHz) spectrometers. The chemical shifts of the fluoro resonances were determined relative to trifluoroacetic acid as the external standard ($CF_3CO_2H$, 0.00 ppm), and the chemical shifts of the phosphorus resonances were determined relative to phosphoric acid as the external standard ($H_3PO_4$: 0.00 ppm). Mass spectra were obtained at Thermo Finnigan LCQ Advantage. Unless otherwise noted, all reactions were conducted in oven—(135° C.) and flame-dried glassware with vacuum-line techniques under an inert atmosphere of dry Ar. THF and $Et_2O$ were distilled from sodium metal dried flask, DCM, pentane, and hexanes were distilled from calcium hydride. Different substituted 2-alkoxystyrene ligands were prepared according to literature procedures as shown in Schemes 1-3. Most chemicals were obtained from commercial sources and confirmed to be used without any quality problems. All product purification was performed with silica gel 60 (200-400 mesh) obtained from Qingdao Haiyang Chemical Co. General procedure is described in example 1 for preparation of different substituted 2-alkoxystyrene ligands 4a-4i, 6a-6n, and 8a-8j by ortho-vinylation reaction (Yamaguchi et al, *J. Org. Chem.* 1998, 63, 7298-7305, synthesis in 50 mmol scale for ortho-vinylation), followed by etherification of 2-hydroxystyrene with alkyliodide or alkylbromide (10 mmol scale for etherification) in DMF in the presence of $K_2CO_3$ at 45-65° C. General procedure is described in example 2 for synthesis of Ru complexes 5a-5i, 7a-7n, and 9a-9j by reaction of Ru complex 1a or 1b with different substituted 2-alkoxystyrene ligands 4a-4l, 6a-6n, and 8a-8j, respectively (Hoveyda et al, *J. Am. Chem. Soc.* 1999, 121, 791-799, and *J. Am. Chem. Soc.* 2000, 122, 8168-8179, synthesis in 0.5 mmol scale). However, based on the general literature procedure as the following Example 2, there is no any product of Ru complex 5a-5l obtained by TLC or flash column. It is observed that the decomposition takes place during the preparation of complexes 5a-5i, which means that the listed Ru complexes 5a-5i are very unstable and impossible to be used as metathesis catalysts.

Example 1

Synthesis of 1-chloro-2-isopropoxy-3-vinyl-benzene (4a)

Preparation of 2-chloro-6-vinylphenol: Ethyne was bubbled into a dichloroethane (DCE, 200 mL) solution of $SnCl_4$ (25 mL, 0.2 mol) and $Bu_3N$ (50 mL, 0.2 mol) at −50° C. for 45 min under an Ar atmosphere, followed by adding 2-chlorophenol (6.50 g, 50 mmol). After finishing the addition, the mixture was heated at 60° C. for 1 hr. $K_2CO_3$ (13.8 g) and methanol (100 mL) were added, and refluxing for another 30 min. After the reaction was completed, the reaction mixture was poured into a mixture of ethyl ether and saturated aq $KHSO_4$. The precipitated byproducts were filtered through Celite, and the organic materials were extracted with ether three times. The combined organic layers were washed with brine and dried over $Na_2SO_4$, then ether was removed by rotovap, 2-chloro-6-vinylphenol was obtained by flash chromatography, 4.83 g of ortho-vinylphenol was obtained (yield: 63%, purity: 97%). The purified ortho-vinylation product could be directly used for next etherification with isopropyliodide (iPrI) in 10 mmol scale.

Preparation of 1-Chloro-2-isopropoxy-3-vinyl-benzene (4a): 2-chloro-6-vinylphenol (1.55 g, 10 mmol) and 2-iodopropane (1.5 ml, 15 mmol, 1.5 equiv) were dissolved in DMF, followed by adding $K_2CO_3$ (3.9 g, 30 mmol) into DMF solution, then heated at 60° C. overnight. etherification was monitored by TLC and HPLC until completed. The mixture was diluted with $Et_2O$ (250 mL), and washed with water (2×200 mL). The aqueous layer was extracted twice with $Et_2O$ (150 mL), and the combined organic layers were washed with brine, and dried over $MgSO_4$. The product was purified by flash column (Hexanes:$Et_2O$=6:1) to offer 1.69 g of product 4a (Yield: 82%, purity: 98%). $^1$HNMR ($CDCl_3$: δ=7.26 ppm): 7.42 (dd, 1H, J=1.56, 7.82 Hz), 7.29 (dd, 1H, J=1.56, 7.83 Hz), 7.02 (m, 2H), 5.73 (d, 1H, J=17.60 Hz), 5.56 (d, 1H, J=11.34 Hz), 4.43 (m, 1H), 1.32 (d, 6H, J=6.26 Hz). (M+H$^+$): m/z calculated: 197.1, found: 197.1.

Example 2

Synthesis of Ruthenium Complex with 1-Chloro-2-isopropoxy-3-vinyl-benzene (5a)

($H_2$IMES)($PCy_3$)$Cl_2$Ru=CHPh (formula 1b) (450 mg, 0.5 mmol) and CuCl (135 mg, 1.25 mmol, 2.5 eq) were added into a 100 mL round-bottom flask under an Ar in a glove box and dissolved in DCM (15 mL), and 1-Chloro-2-isopropoxy-3-vinyl-benzene (4a, 105 mg, 0.5 mmol, 1.0 eq) was added into the red solution at 20-25° C. The reaction was completed and no any 1b left by TLC in 30 min. However, the reaction mixture was dark brown instead of green color for the product of complex 5a, which means that no any green spot of complex 5a was formed and observed by TLC.

Example 3

Synthesis of Ruthenium Complex with 4-Chloro-1-isopropoxy-2-vinyl-benzene (7a)

($H_2$IMES)($PCy_3$)$Cl_2$Ru=CHPh (formula 1b) (450 mg, 0.5 mmol) and CuCl (135 mg, 1.25 mmol, 2.5 eq) were added into a 100 mL round-bottom flask under an Ar in a glove box and dissolved in DCM (15 mL), and 4-Chloro-1-isopropoxy-2-vinyl-benzene (6a, 105 mg, 0.5 mmol, 1.0 eq) was added into the red solution at 20-25° C. The reaction was completed and no any 1b left by TLC in 30 min. The reaction mixture was green color for the product of complex 7a, then filtered. The filtrate was concentrated and purified by flash column eluting with a gradient solvent (Pentane/DCM 2/1 to DCM). Concentration of the product fractions in vacuum resulted in a deep-green solid, which was washed with methanol, and dried under vacuum to give 223 mg of a green microcrystalline solid (68% yield). The green product was confirmed by $^1$HNMR and MS analysis.

$^1$HNMR (400 MHz, $CDCl_3$) δ=16.44 (s, 1H, Ru=CH), 7.46 (dd, 1H, J=2.74, 9.00 Hz), 7.08 (s, 4H), 6.89 (d, 1H, J=2.74 Hz), 6.72 (d, 1H, J=8.61 Hz), 4.85 (m, 1H), 2.46 (s, 12H), 2.41 (s, 6H), 1.25 (d, 6H, J=6.26 Hz). (M+H$^+$): m/z calculated: 661.1; found: 661.2.

Example 4

Synthesis of Ru Complex with 1,2-Dichloro-4-isopropoxy-5-vinyl-benzene (7b)

The synthetic procedure is the same as in Example 3 in 0.5 mmol scale. 203 mg of green solid product was obtained (56% yield).

$^1$HNMR (400 MHz, $CDCl_3$): δ=16.37 (s, 1H, Ru=CH), 7.07 (s, 4H), 6.98 (s, 1H), 6.88 (s, 1H), 4.82 (m, 1H), 4.18 (s, 4H), 2.45 (s, 12H), 2.40 (s, 6H), 1.25 (d, 6H, J=6.26 Hz). (M+H$^+$): m/z calculated: (M+H$^+$): m/z calculated: 695.1; founded: 695.2.

Example 5

Synthesis of Ru Complex with 4-Fluoro-1-isopropoxy-2-vinyl-benzene (7c)

The synthetic procedure is the same as in Example 3 in 0.5 mmol scale. 198 mg of green solid product was obtained (63% yield).

$^1$HNMR (300 MHz, CDCl$_3$): δ=16.49 (s, 1H, Ru=CH), 7.26-7.20 (m, 1H), 7.13 (s, 4H), 6.71 (dd, J=3.0, 9.0 Hz, 1H), 6.62 (dd, J=3.1, 7.9 Hz, 1H), 4.85-4.81 (m, 1H, OCHMe$_2$), 4.19 (s, 4H), 2.47 (s, 12H), 2.27 (s, 6H), 1.26 (d, J=6.2 Hz, 6H). $^{19}$F-NMR (300 MHz, CDCl$_3$): δ=−41.66.

Example 6

Synthesis of Ru Complex with 1,2-Difluoro-4-isopropoxy-5-vinyl-benzene (7d)

The synthetic procedure is the same as in Example 3 in 0.5 mmol scale. 173 mg of green solid product was obtained (51% yield).

$^1$HNMR (300 MHz, CDCl$_3$): δ=16.21 (s, 1H, Ru=CH), 7.07 (s, 4H), 6.72 (t, J=9.4 Hz, 1H), 6.65-6.59 (m, 1H), 4.78-4.74 (m, 1H, OCHMe$_2$), 4.17 (s, 4H), 2.45 (s, 12H), 2.40 (s, 6H), 1.23 (d, J=6.1 Hz, 6H).

Example 7

Synthesis of Ru Complex with 1,5-Difluoro-3-isopropoxy-2-vinyl-benzene (7e)

The synthetic procedure is the same as in Example 3 in 0.5 mmol scale. 152 mg of green solid product was obtained (44% yield).

$^1$H NMR (300 MHz, CDCl$_3$): δ=16.72 (s, 1H), 7.27 (s, 1H), 7.06 (s, 4H), 6.32 (t, 1H, J=10.15 Hz)/6.36-6.28 (m, 2H), 4.80 (m, 1H), 4.18 (s, 4H), 2.47 (s, 12H), 2.37 (s, 6H), 1.28 (d, 6H, J=6.23 Hz).

Example 8

Synthesis of Ru Complex with 4-Isopropoxy-3-vinyl-benzamide (7f)

The synthetic procedure is the same as in Example 3 in 0.5 mmol scale. 213 mg of green solid product was obtained (63% yield).

$^1$H-NMR (300 MHz, CDCl$_3$): δ=16.55 (s, 1H, Ru=CH), 7.93 (d, J=6.9 Hz, 1H), 7.34 (d, J=1.4 Hz, 1H), 7.09 (s, 4H), 6.81 (d, J=8.8 Hz, 1H), 4.94-4.90 (m, 1H, OCHMe$_2$), 4.19 (s, 4H), 2.47 (s, 12H), 2.42 (s, 6H), 1.27 (d, J=5.9 Hz, 6H).

Example 9

Synthesis of Ru Complex with 4-Isopropoxy-3-vinyl-benzoic acid methyl ester (7g)

The synthetic procedure is the same as in Example 3 in 0.5 mmol scale. 197 mg of green solid product was obtained (56% yield).

$^1$HNMR (300 MHz, CDCl$_3$): δ=16.45 (s, 1H, Ru=CH), 8.20 (dd, J=2.2, 8.8 Hz, 1H), 7.63 (d, J=2.2 Hz, 1H), 7.09 (s, 4H), 6.84 (d, J=8.8 Hz, 1H), 4.97-4.93 (m, 1H, OCHMe$_2$), 4.20 (s, 4H), 3.90 (s, 3H), 2.47 (s, 12H), 2.43 (s, 6H), 1.29 (d, J=6.2 Hz, 6H).

Example 10

Synthesis of Ru Complex with 4-Isopropoxy-3-vinyl-benzaldehyde (7h)

The synthetic procedure is the same as in Example 3 in 0.5 mmol scale. 178 mg of green solid product was obtained (52% yield).

$^1$HNMR (300 MHz, CDCl$_3$): δ=16.61 (s, 1H, Ru=CH), 9.89 (s, 1H, CHO), 8.17 (dd, J=2.2, 8.8 Hz, 1H), 7.44 (d, J=2.2 Hz, 1H), 7.09 (s, 4H), 6.95 (d, J=8.8 Hz, 1H), 5.01-4.97 (m, 1H, OCHMe$_2$), 4.19 (s, 4H), 2.47 (s, 12H), 2.43 (s, 6H), 1.31 (d, J=6.3 Hz, 6H).

Example 11

Synthesis of Ru Complex with 1-(4-Isopropoxy-3-vinyl-phenyl)-ethanone (7i)

The synthetic procedure is the same as in Example 3 in 0.5 mmol scale. 189 mg of green solid product was obtained (55% yield).

$^1$HNMR (300 MHz, CDCl$_3$): δ=16.49 (s, 1H, Ru=CH), 8.16 (dd, J=1.9, 8.8 Hz, 1H), 7.53 (d, J=1.9 Hz, 1H), 7.09 (s, 4H), 6.87 (d, J=8.8 Hz, 1H), 4.98-4.94 (m, 1H, OCHMe$_2$), 4.21 (s, 4H), 2.52 (s, 3H), 2.48 (s, 12H), 2.43 (s, 6H), 1.29 (d, J=5.9 Hz, 6H).

Example 12

Synthesis of Ru Complex with (4-Isopropoxy-3-vinyl-phenyl)-phenyl-methanone (7j)

The synthetic procedure is the same as in Example 3 in 0.5 mmol scale. 199 mg of green solid product was obtained (53% yield).

$^1$HNMR (300 MHz, CDCl$_3$): δ=16.39 (s, 1H, Ru=CH), 8.10 (dd, J=1.8, 8.4 Hz, 1H), 7.75-7.72 (m, 2H), 7.63-7.58 (m, 1H), 7.52-7.47 (m, 2H), 7.35 (d, J=1.8 Hz, 1H), 7.02 (s, 4H), 6.92 (d, J=8.4 Hz, 1H), 5.01-4.97 (m, 1H, OCHMe$_2$), 4.19 (s, 4H), 2.46 (s, 12H), 2.24 (s, 12H), 1.29 (d, J=8.1 Hz, 6H).

Example 13

Synthesis of Ru Complex with 4-Isopropoxy-N,N-dimethyl-3-vinyl-benzenesulfonamide (7k)

The synthetic procedure is the same as in Example 3 in 0.5 mmol scale. 247 mg of green solid product was obtained (66% yield).

$^1$HNMR (400 MHz, CDCl$_3$): δ=16.39 (s, 1H, Ru=CH), 7.93 (dd, J=2.2, 8.8 Hz, 1H), 7.32 (d, J=2.2 Hz, 1H), 7.08 (s, 4H), 6.91 (d, J=8.8 Hz, 1H), 4.97-4.94 (m, 1H, OCHMe$_2$), 4.21 (s, 4H), 2.71 (s, 6H), 2.46 (s, 12H), 2.40 (s, 6H), 1.29 (d, J=5.9 Hz, 6H).

Example 14

Synthesis of Ru Complex with Bis-(4-Isopropoxy-3-vinyl-phenyl)-sulfone (7m)

The synthetic procedure is the same as in Example 3 in 0.5 mmol scale. 193 mg of green solid product was obtained (56% yield).

$^1$HNMR (300 MHz, CDCl$_3$): δ=16.42 (s, 2H, Ru=CH), 7.87 (dd, J=2.2, 8.8 Hz, 2H), 7.53 (d, J=2.2 Hz, 2H), 7.07 (s,

8H), 6.87 (d, J=8.8 Hz, 2H), 4.96-4.92 (m, 2H, OCHMe$_2$), 3.15 (s, 8H), 2.45 (s, 24H), 2.41 (s, 12H), 1.27 (d, J=5.9 Hz, 12H).

Example 15

Synthesis of Ru Complex with Bis-(4-isopropoxy-3-vinyl-phenyl)-methanone (7n)

The synthetic procedure is the same as in Example 3 in 0.5 mmol scale. 171 mg of green solid product was obtained (52% yield).
$^1$HNMR (300 MHz, CDCl$_3$): δ=16.44 (s, 2H, Ru=CH), 7.93 (dd, J=2.0, 8.4 Hz, 2H), 7.30 (d, J=2.0 Hz, 2H), 7.03 (s, 8H), 6.88 (d, J=8.4 Hz, 2H), 5.01-4.97 (m, 2H, OCHMe$_2$), 4.19 (s, 8H), 2.47 (s, 24H), 2.26 (s, 12H), 1.33 (d, J=6.2 Hz, 12H).

Example 16

Synthesis of Ru Complex with 1-(4-Isopropoxy-3-vinyl-benzenesulfonyl)-1H-pyrrole (9a)

The synthetic procedure is the same as in Example 3 in 0.5 mmol scale. 211 mg of green solid product was obtained (62% yield).
$^1$HNMR (400 MHz, CDCl$_3$): δ=16.36 (s, 1H, Ru=CH), 7.98 (dd, 1H, J=2.35, 8.81 Hz), 7.40 (d, 1H, J=2.35 Hz), 7.10 (m, 2H), 7.08 (s, 4H), 6.87 (d, 1H, J=9.00 Hz), 6.31 (m, 2H), 4.92 (m, 1H, OCHMe$_2$), 4.20 (s, 4H), 2.44 (s, 18H), 1.13 (d, 6H, J=5.87 Hz).

Example 17

Synthesis of Ru Complex with 4-Isopropoxy-3-methoxy-N,N-dimethyl-5-vinyl-benzenesulfonamide (9b)

The synthetic procedure is the same as in Example 3 in 0.5 mmol scale. 158 mg of green solid product was obtained (41% yield).
$^1$HNMR (300 MHz, CDCl$_3$): δ=16.34 (s, 1H, Ru=CH), 7.45 (d, 1H, J=1.83 Hz), 7.17 (s, 4H), 6.92 (d, 1H, J=2.20 Hz,), 5.80 (m, 1H, OCHMe$_2$), 4.20 (s, 4H), 3.81 (s, 3H), 2.73 (s, 6H), 2.47 (s, 12H), 2.40 (s, 6H), 1.31 (d, 6H, J=6.22 Hz).

Example 18

Synthesis of Ru Complex with 4-(2-Methoxy-ethoxy)-N,N-dimethyl-3-vinyl-benzenesulfonamide (9c)

The synthetic procedure is the same as in Example 3 in 0.5 mmol scale. 165 mg of green solid product was obtained (44% yield).
$^1$HNMR (300 MHz, CDCl$_3$): δ=16.37 (s, 1H, Ru=CH), 7.94 (dd, 1H, J=2.20, 8.79 Hz), 7.29 (d, 1H, J=2.20 Hz), 7.09 (s, 4H), 7.06 (d, 1H, J=8.79 Hz), 4.34 (t, 2H, J=5.85 Hz), 4.18 (s, 4H), 3.61 (t, 2H, J=5.94 Hz), 3.13 (s, 3H), 2.70 (s, 6H), 2.47 (s, 12H), 2.42 (s, 6H).

Example 19

Synthesis of Ru Complex with 1-(4-Isopropoxy-3-vinyl-benzenesulfonyl)-pyrrolidine (9d)

The synthetic procedure is the same as in Example 3 in 0.5 mmol scale. 195 mg of green solid product was obtained (54% yield).
$^1$HNMR (400 MHz, CDCl$_3$): δ=16.39 (s, 1H, Ru=CH), 7.97 (dd, 1H, J=2.35, 8.61 Hz), 7.37 (d, 1H, J=1.96 Hz), 7.08 (s, 4H), 6.90 (d, 1H, J=9.00 Hz), 4.95 (m, 1H, OCHMe$_2$), 4.21 (s, 4H), 3.21 (m, 4H), 2.46 (s, 12H), 2.41 (s, 6H), 1.83 (m, 4H), 1.29 (d, 6H, J=5.87 Hz).

Example 20

Synthesis of Ru Complex with 4-sec-Butoxy-N,N-dimethyl-3-vinyl-benzenesulfonamide (9e)

The synthetic procedure is the same as in Example 3 in 0.5 mmol scale. 176 mg of green solid product was obtained (47% yield).
$^1$HNMR (300 MHz, CDCl$_3$): δ=16.40 (s, 1H, Ru=CH), 7.93 (dd, 1H, J=2.20, 8.79 Hz), 7.33 (d, 1H, J=2.19 Hz), 7.08 (s, 4H), 6.87 (d, 1H, J=8.79 Hz), 4.66 (m, 1H, OCHMe$_2$), 4.21 (s, 4H), 2.72 (s, 6H), 2.47 (s, 12H), 2.42 (s, 6H), 1.45 (m, 2H), 1.27 (d, 3H, J=5.86 Hz), 0.80 (t, 3H, J=7.69 Hz).

Example 21

Synthesis of Ru Complex with 1-(4-Isopropoxy-3-vinyl-benzenesulfonyl)-pyrrolidine-2-carboxylic acid methyl ester (9f)

The synthetic procedure is the same as in Example 3 in 0.5 mmol scale. 196 mg of green solid product was obtained (52% yield).
$^1$HNMR (400 MHz, CDCl$_3$): δ=16.39 (s, 1H, Ru=CH), 8.04 (dd, 1H, J=1.95, 8.60 Hz), 7.41 (d, 1H, J=2.35 Hz), 7.10 (s, 4H), 6.89 (d, 1H, J=8.61 Hz), 4.95 (m, 1H, OCHMe$_2$), 4.24 (m, 1H), 4.21 (s, 4H), 3.66 (s, 3H), 3.48 (m, 1H), 3.24 (m, 1H), 2.46 (s, 12H), 2.42 (s, 6H), 1.81-2.13 (m, 5H), 1.28 (d, 6H, J=5.87 Hz).

Example 22

Synthesis of Ru Complex with 1-(4-Isopropoxy-3-vinyl-benzenesulfonyl)-piperidine-4-carboxylic acid methyl ester (9g)

The synthetic procedure is the same as in Example 3 in 0.5 mmol scale. 226 mg of green solid product was obtained (55% yield).
$^1$HNMR (300 MHz, CDCl$_3$): δ=16.39 (s, 1H, Ru=CH), 7.90 (dd, 1H, J=2.20, 8.79 Hz), 7.30 (d, 1H, J=1.83 Hz), 7.08 (s, 4H), 6.90 (d, 1H, J=8.79 Hz,), 4.95 (m, 1H, OCHMe$_2$), 4.21 (s, 4H), 3.69 (s, 3H), 3.63 (m, 1H), 2.47 (s, 12H), 2.41 (s, 6H), 2.09 (dd, 4H, J=3.29, 13.55 Hz), 1.85 (m, 4H), 1.30 (d, 6H, J=6.22 Hz).

Example 23

Synthesis of Ru Complex with 4-(4-Isopropoxy-3-vinyl-benzenesulfonyl)-morpholine (9h)

The synthetic procedure is the same as in Example 3 in 0.5 mmol scale. 193 mg of green solid product was obtained (52% yield).
$^1$HNMR (300 MHz, CDCl$_3$): δ=16.31 (s, 1H, Ru=CH), 7.83 (dd, 1H, J=2.19, 8.79 Hz), 7.24 (d, 1H, J=2.20 Hz), 7.00 (s, 4H), 6.85 (d, 1H, J=8.79 Hz), 4.89 (m, 1H, OCHMe$_2$), 4.13 (s, 4H), 3.68 (t, 4H, J=4.77 Hz), 2.95 (t, 4H, J=4.76 Hz), 2.39 (s, 12H), 2.33 (s, 6H), 1.23 (d, 6H, J=6.23 Hz).

Example 24

Synthesis of Ru Complex with 4-Isopropoxy-N,N-dipropyl-3-vinyl-benzenesulfonamide (9i)

The synthetic procedure is the same as in Example 3 in 0.5 mmol scale. 216 mg of green solid product was obtained (54% yield).

$^1$HNMR (300 MHz, CDCl$_3$): δ=16.36 (s, 1H, Ru=CH), 7.90 (dd, 1H, J=2.20, 8.79 Hz), 7.32 (d, 1H, J=2.20 Hz), 7.09 (s, 4H), 6.88 (d, 1H, J=8.78 Hz), 4.66 (m, 1H, OCHMe$_2$), 4.21 (s, 4H), 3.77 (t, 4H, J=4.76 Hz), 3.03 (t, 4H, J=4.84), 2.47 (s, 12H), 2.42 (s, 6H), 1.38 (m, 2H), 1.30 (d, 3H, J=9.15 Hz), 0.90 (t, 3H, J=7.69 Hz).

Example 25

Synthesis of Ru Complex with 4-(4-sec-Butoxy-3-vinyl-benzenesulfonyl)-morpholine (9j)

The synthetic procedure is the same as in Example 3 in 0.5 mmol scale. 186 mg of green solid product was obtained (47% yield).

$^1$HNMR (300 MHz, CDCl$_3$): δ=16.36 (s, 1H, Ru=CH), 7.90 (dd, 1H, J=2.20, 8.79 Hz), 7.32 (d, 1H, J=2.20 Hz), 7.09 (s, 4H), 6.88 (d, 1H, J=8.78 Hz), 4.66 (m, 1H, OCHMe$_2$), 4.21 (s, 4H), 3.77 (t, 4H, J=4.76 Hz), 3.03 (t, 4H, J=4.84), 2.47 (s, 12H), 2.42 (s, 6H), 1.48 (m, 2H), 1.30 (d, 3H, J=9.15 Hz), 0.80 (t, 3H, J=7.69 Hz).

Example 26

Synthesis of 1-(4-Isopropoxy-3-vinyl-benzenesulfonyl)-piperidine-4-carboxylic acid (15)

Compound 8g (2.0 g, 5.0 mmol) was dissolved in 30 mL MeOH and 15 mL water, and NaOH (1.0 g, 25.0 mmol) was added, the reaction mixture was stirred at 20° C. for 4.0 hrs. The solvent was removed rotovap, 30 mL water was added and the mixture was extracted with ether (2×70 mL) and the aqueous phase was adjusted to pH=2-3, then extracted with EtOAc (3×60 mL) and the combined organic phase was washed with brine, dried and concentrated. 1.7 g of product 15 was obtained in 92% of yield (Purity: 98%).

$^1$HNMR (300 MHz, CDCl$_3$): δ=7.80 (d, 1H, J=2.47 Hz), 7.60 (dd, 1H, J=2.47, 8.79 Hz), 7.00 (dd, 1H, J=11.26, 17.85 Hz), 6.95 (d, 1H, J=8.79 Hz), 5.81 (dd, 1H, J=1.1, 17.58 Hz), 5.39 (dd, 1H, J=1.1, 11.27 Hz), 4.66 (m, 1H), 3.64 (m, 2H), 2.43 (m, 2H), 2.26 (m, 1H), 2.00 (m, 2H), 1.87 (m, 2H), 1.42 (d, 6H, J=6.05 Hz). (M+H$^+$): m/z calculated: 352.1, found: 352.1.

Example 27

Synthesis of Resin Bounded Ru Catalyst (19a)

To the solution of compound 15 (0.80 g, 2.3 mmol) in DCM (20 mL) was added HOBt (0.32 g, 2.4 mmol), then DCC (0.52 g, 2.5 mmol) in DCM (8 mL) was added dropwise, the resulting mixture was stirred overnight. Filtrated and concentrated. 1.20 g of product was obtained, and added to a DMF solution (15 mL) of polystyrene resin (0.85 g, 1.44 mmol, 1.0 eq.) and DMAP (0.2 g, 1.44 mmol, 1.0 eq.). The reaction mixture was shaked overnight. After the coupling was completed, the resin was washed with DMF (20 mL×3), THF (20 mL×3), DCM (20 mL×3), 1/1 DCM/Et$_2$O (20 mL×1), Et$_2$O (20 mL×3) and dried under reduced pressure to offer 0.98 g of product 16a.

To a solution of 16a (0.90 g, 1.5 mmol, 1.0 eq.) in DCM (15 mL), (PPh$_3$)$_2$Cl$_2$Ru=CHPh (1.95 g, 2.25 mmol, 1.5 eq.) and CuCl (0.39 g, 3.75 mmol, 2.5 eq.) were added under Ar. The solution was agitated for 2 hrs to offer product 17a, followed by adding PCy3 (2.0 eq) in DCM (5 mL) at −60° C. for 30 min, then kept agitating overnight. The resin was washed with DMF (20 mL×3), THF (20 mL×3), DCM (20 mL×3), 1/1 DCM/Et$_2$O (20 mL×1), Et$_2$O (20 mL×3) and dried to offer 1.24 g of product 18a.

To a solution of 18a (0.90 g, 1.5 mmol, 1.0 eq.) in DCM (5 mL) was added into another ligand H$_2$IMes(H)(CCl$_3$) solution in toluene (10 mL) at 80° C. with agitation and kept overnight until the reaction was completed. The resin was washed with DMF (20 mL×3), THF (20 mL×3), DCM (20 mL×3), 1/1 DCM/Et$_2$O (20 mL×1), Et$_2$O (20 mL×3) and dried to offer 1.11 g of product 19a.

IR: 3454.20 (w), 2921.47 (br), 1733.20 (m), 1613.66 (s), 1112.85 (m).

Example 28

Synthesis of Resin Bounded Ru Catalyst (19b)

The synthetic procedure is the same as in Example 27 starting with 0.8 g of 15 and PEG800 (1.0 eq) to obtain 16b, followed by reacting with (PPh$_3$)$_2$Cl$_2$Ru=CHPh (1.eq) and CuCl (3.0 eq) in DCM for 2 hr to form 17b, then PCy3 (2.0 eq) was added to offer 18b. Finally, 18b (0.50 g) in DCE (5 mL) was added into another prepared H$_2$IMes carbene solution in toluene (10 mL), and kept shaking overnight, then purified by flash column to obtain 0.36 g of product 19b as dark green solid.

$^1$HNMR (300 MHz, CDCl$_3$): δ=16.38 (s, 1H, Ru=CH), 7.92 (dd, 1H, J=2.20, 8.79 Hz), 7.30 (d, 1H, J=1.83 Hz), 7.08 (s, 4H), 6.90 (d, 1H, J=8.79 Hz,), 4.95 (m, 1H, OCHMe$_2$), 4.21 (s, 4H), 3.70-1.30 (broad peaks, PEG proton peaks overlapped).

IR: 3441.82 (w), 2925.79 (m), 1732.10 (s), 1633.66 (s), 1263.83 (s), 1106.00 (m).

Example 29

Synthesis of 2-Isopropoxy-5-chlorobenzaldehyde p-Toluenesulfonydrazone (27a)

A suspension of p-toluenesulfonyl hydrazide (26.5 g, 142 mmol, 1.0 eq.) in methanol (100 mL) was treated rapidly with aldehyde 26a (29 g, 145 mmol, 1.0 eq.) under agitation. After 30 min, the solution was cooled to 0-5° C., and product was precipitated, filtered, and dried to offer a white solid product 27a (50.4 g, 96% yield, purity: 99%).

$^1$HNMR (300 MHz, CDCl$_3$): δ=8.08 (d, J=1.6 Hz, 1H), 7.88 (d, J=8.5 Hz, 1H), 7.77 (d, J=2.8 Hz, 2H), 7.33 (d, J=7.9 Hz, 1H), 7.25 (dd, J=2.8, 7.9 Hz, 1H), 6.79 (d, J=8.8 Hz, 2H), 4.52-4.48 (m, 1H, OCHMe$_2$), 2.42 (s, 3H), 1.29 (d, J=6.1 Hz, 6H). (M+H$^+$): m/z calculated: 366.1; found: 366.1.

Example 30

Synthesis of Ru Complex with PPh$_3$ and 5-Chloro-2-isopropoxybenzylidene Ligand (28a)

27a (10 g, 27.3 mmol, 1.0 eq) was treated with NaOEt (3.9 g, 54.6 mmol, 2.0 eq.) in EtOH (100 mL) and heated to 60° C. After the reaction was completed in 50 min, ice water (120 mL) was added, and extracted with pentane (3×100 mL). The combined organic solution was washed with saturated Na$_2$CO$_3$ (50 mL×2), brine (50 mL×2), and dried with Na$_2$SO$_4$, then concentrated at 0-5° C. to about 20 mL, followed by adding the concentrated diazo solution into the RuCl$_2$(PPh$_3$)$_3$ (7.0 g, 7.3 mmol, 1.0 eq.) solution in CH$_2$Cl$_2$ (50 mL) at −78° C. After 10-15 min, the solution was warmed up to 20° C., and CuCl (2.2 g, 21.9 mmol, 3.0 eq.) was added to react for another 15 min, then the reaction mixture was filtered, and the filtrate was concentrated and purified by flash column eluting with a gradient solvents (2:1 hexane/DCM to DCM). Concentration of the product fractions offers a deep-green solid, which was washed with hexanes, dried under vacuum to give 2.9 g of 28a as a red microcrystalline solid (64% yield).

$^1$HNMR (300 MHz, CDCl$_3$): δ=16.60 (d, J$_{PH}$=6.8 Hz, 1H, Ru=CH), 7.63-7.44 (m, 17H), 7.14 (d, J=8.5 Hz, 1H), 5.41-5.38 (m, 1H, OCHMe$_2$), 1.90 (d, J=6.4 Hz, 6H). $^{31}$P-NMR (121 MHz, CDCl$_3$): δ=56.350 (s, PPh$_3$).

Example 31

Synthesis of Ru Complex with H$_2$IMes and 5-Chloro-2-isopropoxybenzylidene Ligand (30a)

H$_2$IMes(H)(CCl$_3$) (1.38 g, 3.24 mmol, 2.0 eq.) and 28a (1.0 g, 1.62 mmol, 1.0 eq.) was dissolved in toluene (10 mL) and heated to 80° C. for 2.0 h, then cooled. The solution was purified by flash column eluting with 2:1 hexane/DCM. Concentration of the product fractions in vacuum resulted a deep-green solid, which was washed with methanol and hexanes, dried under vacuum to offer 533 mg of product 30a as a green microcrystalline solid (51% yield).

$^1$HNMR (300 MHz, CDCl$_3$): δ=16.46 (s, 1H, Ru=CH), 7.46 (dd, J=2.6, 8.7 Hz, 1H), 7.08 (s, 4H), 6.89 (d, J=2.6 Hz, 1H), 6.72 (d, J=8.7 Hz, 1H), 4.88-4.82 (m, 1H, OCHMe$_2$), 4.18 (s, 4H), 2.46 (s, 12H), 2.41 (s, 6H), 1.25 (d, J=6.2 Hz, 6H).

Example 32

Synthesis of 2-Isopropoxy-5-fluorobenzaldehyde p-Toluenesulfonydrazone (27b)

The synthetic procedure is the same as in Example 29 for preparation of 27a. The yield for 27b is 95%, and the NMR results for 27b are as follows:

$^1$HNMR (300 MHz, CDCl$_3$): δ=8.10 (d, J=1.9 Hz, 1H), 7.97 (s, 1H), 7.87 (d, J=8.2 Hz, 2H), 7.50 (dd, J=3.0, 9.0 Hz, 1H), 7.32 (d, J=8.2 Hz, 2H), 7.02-6.95 (m, 1H), 6.80 (dd, J=4.4, 9.1 Hz, 1H), 4.53-4.42 (m, 1H), 2.41 (s, 3H), 1.29 (d, J=6.1 Hz, 6H). $^{19}$F-NMR (282 MHz, CDCl$_3$): δ=−40.25. (M+H$^+$): m/z calculated: 350.1; found: 350.2.

Example 33

Synthesis of Ru Complex with PPh$_3$ and 5-Fluoro-2-isopropoxybenzylidene Ligand (28b)

The synthetic procedure is the same as in Example 30. The yield for 28b is 57%, and the NMR results for 28b are as follows:

$^1$HNMR (300 MHz, CDCl$_3$): δ=16.59 (d, J$_{PH}$=6.6 Hz, 1H, Ru=CH), 7.55-7.26 (m, 17H), 7.09 (dd, J=3.9, 9.0 Hz, 1H), 5.37-5.32 (m, 1H, OCHMe$_2$), 1.86 (d, J=6.3 Hz, 6H). $^{19}$F-NMR (282 MHz, CDCl$_3$): δ=−40.48. $^{31}$P-NMR (121 MHz, CDCl$_3$): δ=56.19 (s, PPh$_3$).

Example 34

Synthesis of Ru Complex with H$_2$IMes and 5-Fluoro-2-isopropoxybenzylidene Ligand (30b)

The synthetic procedure is the same as in Example 31. The yield for 30b is 42%, and the NMR results for 30b are as follows:

$^1$HNMR (300 MHz, CDCl$_3$): δ=16.49 (s, 1H, Ru=CH), 7.26-7.20 (m, 1H), 7.13 (s, 4H), 6.71 (dd, J=3.0, 9.0 Hz, 1H), 6.62 (dd, J=3.1, 7.9 Hz, 1H), 4.85-4.81 (m, 1H, OCHMe$_2$), 4.19 (s, 4H), 2.47 (s, 121H), 2.27 (s, 6H), 1.26 (d, J=6.2 Hz, 6H). $^{19}$F-NMR (282 MHz, CDCl$_3$): δ=−41.663.

Example 35

Synthesis of 2-Isopropoxy-5-dimethylaminosulfonylbenzaldehyde p-Toluenesulfonydrazone (32a)

The synthetic procedure is the same as in Example 29 for preparation of 27a. The yield for 32a is 96%, and the NMR result of 32a is as follows:

$^1$HNMR (300 MHz, CDCl$_3$): δ=8.14-8.11 (m, 2H), 7.87 (d, J=8.2 Hz, 2H), 7.71-7.67 (m, 1H), 7.30 (d, J=8.2 Hz, 2H), 6.94 (d, J=8.8 Hz, 1H), 4.68-4.60 (m, 1H, OCHMe$_2$), 2.70 (s, 6H), 2.40 (s, 3H), 1.35 (d, J=6.0 Hz, 6H). (M+H$^+$): m/z calculated: 439.1; found: 439.2.

Example 36

Synthesis of Ru Complex with PPh$_3$ and 2-Isopropoxy-5-dimethylaminosulfonylbenzylidene Ligand (33a)

The synthetic procedure is the same as in Example 30 for preparation of 28a. The yield for 33a is 63%, and the NMR results of 33a are as follows:

$^1$HNMR (300 MHz, CDCl$_3$): δ=16.69 (d, J$_{PH}$=6.9 Hz, 1H, Ru=CH), 8.09-8.06 (m, 2H), 7.57-7.43 (m, 16H), 7.34 (d, J=9.0 Hz, 1H), 5.53-5.49 (m, 1H, OCHMe$_2$), 2.82 (s, 6H), 1.94 (d, J=6.4 Hz, 6H). $^{31}$P-NMR (121 MHz, CDCl$_3$) δ=56.05 (s, PPh$_3$).

Example 37

Synthesis of Ru Complex with PCy$_3$ and 2-Isopropoxy-5-dimethylaminosulfonylbenzylidene Ligand (34a)

33a (4.0 g, 5.8 mmol, 1.0 eq.) was dissolved in CH$_2$Cl$_2$ (50 mL) under Ar, then tricyclohexylphosphine (PCy$_3$, 3.25 g, 11.6 mmol, 2.0 eq.) was added. The solution was stirred at 20° C. for 0.5 h, then concentrated and purified by flash column eluting with a gradient solvent (2:1 petroleum ether/DCM to DCM). Concentration in vacuum resulted a brown solid, which was washed with methanol, dried under vacuum resulted 2.76 g of product 34a as a purple microcrystalline solid (67% yield).

$^1$HNMR (300 MHz, CDCl$_3$): δ=17.40 (d, J$_{PH}$=4.3 Hz, 1H, Ru=CH), 8.13 (d, J=2.1 Hz, 1H), 8.04 (dd, J=2.1, 8.6 Hz,

1H), 7.21 (d, J=8.6 Hz, 1H), 5.36-5.30 (m, 1H, OCHMe$_2$), 2.79 (s, 6H), 2.39-1.28 (m, 39H). $^{31}$P-NMR (121 MHz, CDCl$_3$): δ=55.91 (s, PCy$_3$).

Example 38

Synthesis of Ru Complex with H$_2$IMes and 2-Isopropoxy-5-dimethylaminosulfonylbenzylidene Ligand (7k)

H$_2$IMes(H)(CCl$_3$) (1.4 g, 3.2 mmol, 2.0 eq.) and 34a (1.2 g, 1.6 mmol, 1.0 eq.) was dissolved in toluene (10 mL) and heated to 80° C. for 1.5 h, then cooled. The solution was purified by flash column eluting with 2:1 hexane/DCM. Concentration of the product fractions in vacuum resulted a deep-green solid, which was washed with methanol and hexanes, dried under vacuum to offer 685 mg of product 7k as a green microcrystalline solid (58% yield).

$^1$HNMR (300 MHz, CDCl$_3$): δ=16.39 (s, 1H, Ru=CH), 7.93 (dd, J=2.2, 8.8 Hz, 1H), 7.32 (d, J=2.2 Hz, 1H), 7.08 (s, 4H), 6.91 (d, J=8.8 Hz, 1H), 4.97-4.94 (m, 1H, OCHMe$_2$), 4.21 (s, 4H), 2.71 (s, 6H), 2.46 (s, 12H), 2.40 (s, 6H), 1.29 (d, J=5.9 Hz, 6H).

Example 39

Synthesis of 2-Isopropoxy-5-nitrobenzaldehyde p-Toluenesulfonylhydrazone (32b)

The synthetic procedure is the same as in Example 29 for preparation of 27a. The yield for 32b is 93%, and the NMR result of 32b is as follows:

$^1$H-NMR (300 MHz, CDCl$_3$): δ=8.62 (d, J=3.0 Hz, 1H), 8.18 (dd, J=3.0, 9.4 Hz, 1H), 8.16 (s, 1H), 7.91 (d, J=8.3 Hz, 2H), 7.36 (d, J=8.3 Hz, 2H), 6.91 (d, J=9.4 Hz, 1H), 4.74-4.66 (m, 1H, OCHMe$_2$), 2.42 (s, 3H), 1.38 (d, J=6.0 Hz, 6H). (M+H$^+$): m/z calculated: 378.1; found: 378.1.

Example 40

Synthesis of Ru Complex with PPh$_3$ and 2-Isopropoxy-5-nitrobenzylidene Ligand (33b)

The synthetic procedure is the same as in Example 30 for preparation of 28a. The yield for 33b is 66%, and the NMR result of 33b is as follows:

$^1$HNMR (300 MHz, CDCl$_3$): δ=16.62 (d, J$_{PH}$=6.8 Hz, 1H, Ru=CH), 8.53 (dd, J=2.6, 9.0 Hz, 1H), 7.55-7.39 (m, 16H), 7.27 (d, J=9.0 Hz, 1H), 5.52-5.47 (m, 1H, OCHMe$_2$), 1.91 (d, J=6.0 Hz, 6H).

Example 41

Synthesis of Ru Complex with PCy$_3$ and 2-Isopropoxy-5-nitrobenzylidene Ligand (34b)

The synthetic procedure is the same as in Example 37 for preparation of 34a. The yield for 34b is 71%, and the NMR result of 34b is as follows:

$^1$HNMR (300 MHz, CDCl$_3$): δ=17.38 (d, J$_{PH}$=4.7 Hz, 1H, Ru=CH), 8.53 (dd, J=2.6, 8 Hz, 1H), 7.49 (m, 1H), 7.27 (d, J=8.0 Hz, 1H), 5.37 (m, 1H, OCHMe$_2$), 2.35-1.26 (m, 39H).

Example 42

Synthesis of Ru Complex with H$_2$IMes and 2-Isopropoxy-5-nitrobenzylidene Ligand (10e)

The synthetic procedure is the same as in Example 38 for preparation of complex 7k. The yield for 10e is 61%, and the NMR result of 10e is as follows:

$^1$HNMR (300 MHz, CDCl$_3$): δ=16.47 (s, 1H, Ru=CH), 8.43 (dd, J=2.5, 9.2 Hz, 1H), 7.82 (d, J=2.5 Hz, 1H), 7.10 (s, 4H), 6.89 (d, J=9.2 Hz, 1H), 5.01-4.95 (m, 1H, OCHMe$_2$), 4.22 (s, 4H), 2.46 (s, 12H), 2.44 (s, 6H), 1.30 (d, J=6.2 Hz, 6H).

Example 43

Synthesis of Ru Complex with PCy$_3$ and 4-(4-Isopropoxy-3-vinyl-benzenesulfonyl)-morpholine Ligand (35a)

The synthetic procedure is the same as in Example 37 for preparation of 34a. The yield for 35a is 68%, and the NMR result of 35a is as follows:

$^1$HNMR (300 MHz, CDCl$_3$): δ=17.38 (d, 1H, J=4.39 Hz), 8.12 (d, 1H, J=2.20 Hz,), 8.01 (dd, 1H, J=2.20, 8.79 Hz), 7.22 (d, 1H, J=8.79 Hz), 5.35 (m, 1H), 3.79 (t, 4H, J=4.77 Hz), 3.11 (t, 4H, J=4.76 Hz), 2.35-1.29 (m, 39H).

Example 44

Synthesis of Ru Complex with PCy$_3$ and 4-(4-sec-Butoxy-3-vinyl-benzenesulfoniyl)-morpholine Ligand (35b)

The synthetic procedure is the same as in Example 37 for preparation of 34a. The yield for 35b is 57%, and the NMR results of 35b are as follows:

$^1$HNMR (300 MHz, CDCl$_3$): δ=17.38 (d, J=4.4 Hz, 1H, Ru=CH), 8.11 (d, J=1.8 Hz, 1H), 8.00 (dd, J=1.8, 8.7 Hz, 1H), 7.17 (d, J=8.7 Hz, 1H), 5.06-5.01 (m, 1H, OCH), 3.78 (t, J=4.7 Hz, 4H), 3.11 (t, J=4.7 Hz, 4H), 2.44-1.03 (m, 41H, PCy$_3$, O-$^i$Bu)). $^{31}$P-NMR (121 MHz, CDCl$_3$): δ=56.039 (s, PCy$_3$).

Example 45

RCM, Selecting the Ru Complexes of Examples 3-44 as Catalyst

General Procedure for RCM Catalyzed by Ru Complex in DCM: Olefin substrate (11, 13, 20, 22, 34, 36, or 38, 50 mg/each, respectively) was dissolved in 1.0 mL of freshly distilled DCM in a 15 mL two-neck round-bottom flask under Ar at 20-25° C., then Ru catalyst (2 mol % of 7a-7k or 9a-9j, respectively) was added into the DCM solution. The kinetic data for conversion of RCM reactions in Equations 1-7 were determined by HPLC at 10 min., 30 min. 1.5 hr, 3.0 hr, until completed overnight. The RCM product (12, 14, 21, 23, 35, 37, or 39, respectively) was determined and the conversion results of RCM reactions were listed in Tables 1-4, respectively.

12: $^1$HNMR (400 MHz, CDCl$_3$): δ=7.78 (d, 2H, J=8.21 Hz), 7.31 (m, 7H), 6.01 (m, 1H), 4.47 (m, 2H), 4.30 (m, 2H), 2.41 (s, 3H). (M+H$^+$): m-/z calculated: 300.1, found: 300.2.

14: $^1$HNMR (400 MHz, CDCl$_3$): δ=7.15 (d, 1H, J=2.74 Hz), 6.84 (d, 1H, J=2.34 Hz), 6.34 (dt, 1H, J=1.95, 9.78 Hz), 5.86 (d, 1H, J=9.78 Hz), 4.95 (m, 2H). (M+H$^+$): m/z calculated: 200.99, found: 201.1.

23: ¹HNMR (400 MHz, CDCl₃): δ=7.70 (d, 2H, J=8.19 Hz), 7.31 (d, 1H, J=8.61 Hz), 5.21 (d, 1H, J=1.17 Hz), 4.06 (m, 2H), 3.96 (s, 2H), 2.42 (s, 3H), 1.70 (s, 3H). (M+H⁺): m/z calculated: 238.1; found: 238.2.

37: ¹HNMR (300 MHz, CDCl₃): δ=7.72 (d, J=8.2 Hz, 1H), 7.32 (d, J=8.0 Hz, 1H), 5.66 (d, J=4.4 Hz, 1H), 4.11 (d, J=4.4 Hz, 1H), 2.42 (s, 3H). m/z calculated: 222.1; found: 222.2.

Example 46

CM, Selecting the Ru Complexes of 9a and 9d as Catalyst

General Procedure for Cross Metathesis (CM) Catalyzed by Ru Complex in DCM: Olefin substrate (24, 50 mg) was dissolved in 1.0 mL of freshly distilled DCM in a 15 mL two-neck round-bottom flask under Ar at 20-25° C., then Ru catalyst (2 mol % of 19a or 19b, respectively) was added into the DCM solution. The kinetic data for conversion of RCM reaction was determined by HPLC at 10 min., 30 min. 1.5 hr, 3.0 hr, until completed overnight. The RCM product 25 was determined in high yield and the conversion results of RCM reactions was listed in Equation 5.

25: ¹HNMR (400 MHz, CDCl₃): δ=7.54 (d, 4H, J=7.24 Hz), 7.39 (t, 4H, J=7.43 Hz), 7.28 (t, 2H, J=7.43 Hz), 7.14 (s, 2H). (M+H⁺): m/z calculated: 181.1, found: 181.2.

What is claimed is:

1. A ruthenium catalyst having the following structure I:

I wherein:
X¹ and X² are the same or different and each selected from electron-withdrawing anionic ligands, wherein X¹ and X² may be linked to each other via carbon-carbon and/or carbon-heteroatom bonds;
Y is a neutral two-electron donor selected from oxygen, sulfur, nitrogen or phosphorus;
R is H, halogen atom, alkyl, alkoxy, aryl, aryloxy, alkylcarbonyl, arylcarbonyl, alkoxycarbonyl, aryloxycarbonyl, heteroaryl, carboxyl (RCO₂—), cyano, nitro, amido, amino, aminosulfonyl, N-heteroarylsulfonyl, alkylsulfonyl, arylsulfonyl, alkylsulfinyl, arylsulfinyl, alkylthio, arylthio, or sulfonamido group;
R¹ and R² are each H, Br, I, alkyl, alkoxy, aryl, aryloxy, alkylcarbonyl, arylcarbonyl, alkoxycarbonyl, aryloxycarbonyl, carboxyl, amido, amino, heteroaryl, alkylthio, arylthio, or sulfonamido group;
R³ is an alkyl, aryl, heteroaryl, alkylcarbonyl, arylcarbonyl, thiocarbonyl, or aminocarbonyl group;
EWG is an electron withdrawing group and selected from aminosulfonyl, amidosulfonyl, aryloxycarbonyl, or aminocarbonyl; and
L is an electron donating ligand, which may be linked to X¹ via carbon-carbon and/or carbon-heteroatom bonds.

2. The ruthenium catalyst according to claim 1, wherein X¹ and X² are each selected from an anionic ligand of halides, carboxylates, or aryloxides.

3. The ruthenium catalyst according to claim 2, wherein X¹ and X² each is a halogen.

4. The ruthenium catalyst according to claim 3, wherein X¹ and X² each is chloride (Cl).

5. The ruthenium catalyst according to claim 1, wherein Y is oxygen (O).

6. The ruthenium catalyst according to claim 1, wherein R is H, halogen atom, alkoxycarbonyl, aryloxycarbonyl, heteroaryl, carboxyl, amido, alkylsulfonyl, arylsulfonyl, alkylthio, arylthio, or sulfonamido group.

7. The ruthenium catalyst according to claim 6, wherein R is H, Cl, F, or $C_{1-8}$ alkoxycarbonyl group.

8. The ruthenium catalyst according to claim 1, wherein R¹ and R² each is H, alkoxy, aryl, aryloxy, alkoxycarbonyl, amido, alkylthio, arylthio, or sulfonamido group.

9. The ruthenium catalyst according to claim 8, wherein R¹ is H or alkoxy group, and R² is H.

10. The ruthenium catalyst according to claim 1, wherein R³ is an alkyl, aryl, heteroaryl, alkylcarbonyl, or arylcarbonyl group.

11. The ruthenium catalyst according to claim 10, wherein R³ is isopropyl, sec-butyl, or methoxyethyl.

12. The ruthenium catalyst according to claim 1, wherein EWG is aminosulfonyl, or aminocarbonyl.

13. The ruthenium catalyst according to claim 12, wherein EWG is $C_{1-12}$ N-alkylaminosulfonyl, or $C_{6-12}$ aryloxycarbonyl.

14. The ruthenium catalyst according to claim 1, wherein L is an electron donating ligand selected from phosphine, amino, aryloxides, carboxylates; or heterocyclic carbene group, which may be linked to X¹ via carbon-carbon and/or carbon-heteroatom bonds.

15. The ruthenium catalyst according to claim 14, wherein L is heterocyclic carbene ligand or phosphine $P(R^8)_2(R^9)$ having the following structure IIa, IIb, IIc, or IId:

IIa

IIb

IIc

IId wherein:
R⁴ and R⁵ each is $C_{6-12}$ aryl; and
R⁶ and R⁷ each is H, halogen, alkyl, alkoxy, aryl, aryloxy, alkylcarbonyl, arylcarbonyl, alkoxycarbonyl, aryloxycarbonyl, heteroaryl, carboxyl, cyano, nitro, amido, amino, alkylsulfonyl, arylsulfonyl, alkylsulfinyl, arylsulfinyl, alkylthio, arylthio, or sulfonamido group; and $R^8$ and $R^9$ each is $C_{1-8}$ alkyl or $C_{6-12}$ aryl.

16. The ruthenium catalyst according to claim 15, wherein L is IIa or IId, $R^4$ and $R^5$ each is 2,4,6-trimethylphenyl (mesityl), $R^6$ and $R^7$ each is H, and $R^8$ and $R^9$ each is cyclohexyl (Cy).

17. A method of carrying out a metathesis reaction, comprising an intramolecular RCM reaction and intermolecular CM or ROMP reaction in the presence of the catalyst of claim 1.

18. A method of making a polymer, comprising reacting one or more monomers in the presence of the catalyst of claim 1.

19. The ruthenium catalyst according to claim 15, wherein EWG is amidosulfonyl.

20. The ruthenium catalyst according to claim 15, wherein EWG is aryloxycarbonyl.

21. The ruthenium catalyst according to claim 15, wherein EWG is aminocarbonyl.

* * * * *